United States Patent [19]

Yiv

[11] Patent Number: 5,707,648
[45] Date of Patent: Jan. 13, 1998

[54] TRANSPARENT LIQUID FOR ENCAPSULATED DRUG DELIVERY

[75] Inventor: Seang H. Yiv, Wilmington, Del.

[73] Assignee: LDS Technologies, Inc., Boothwyn, Pa.

[21] Appl. No.: 406,935

[22] PCT Filed: Nov. 16, 1994

[86] PCT No.: PCT/US94/13394

§ 371 Date: May 17, 1995

§ 102(e) Date: May 17, 1995

[87] PCT Pub. No.: WO95/14037

PCT Pub. Date: May 26, 1995

Related U.S. Application Data

[63] Continuation-in-part of Ser. No. 153,846, Nov. 17, 1993, abandoned.

[51] Int. Cl.$^6$ .................... A61K 9/127; B01J 13/02; B32B 5/16
[52] U.S. Cl. .................. 424/450; 264/4.1; 428/402.21
[58] Field of Search .................. 424/450; 264/4.1; 428/402.21

[56] References Cited

U.S. PATENT DOCUMENTS

| | | | |
|---|---|---|---|
| 4,695,450 | 9/1987 | Bauer et al. | 424/22 |
| 5,002,771 | 3/1991 | Purkaystha et al. | 424/433 |
| 5,026,825 | 6/1991 | Grebow et al. | 530/307 |
| 5,037,653 | 8/1991 | Dawson | 424/405 |
| 5,045,337 | 9/1991 | El-Nokaly | 426/602 |
| 5,206,219 | 4/1993 | Desai | 514/3 |

FOREIGN PATENT DOCUMENTS

| | | |
|---|---|---|
| WO 93/06921 | 10/1991 | WIPO. |
| PCT/US93/09915 | 10/1993 | WIPO. |
| PCT/US93/09916 | 10/1993 | WIPO. |
| PCT/US93/09963 | 10/1993 | WIPO. |

OTHER PUBLICATIONS

Wakerly, M.G., "Self-Emulsifying Drug Delivery Systems based on Nonionic Surfactant-Oil Mixtures" University of Bath (1989).

Rizzo, V., Hydrophilic Molecules Solubilized in Water-in-Oil Microemulsions: Distribution of Species in a Chemical Equilibrium, Journal of Colloid and Interface Science, pp. 110-113, vol. 110, No. 1, Mar. 1986.

Fletcher, P.D.L. et al, The Partitioning of Proteins Between Water-In-Oil Microemulsions and Conjugate Aqueous Phases, J. Chem. Soc., Faraday Trans. 1, 1988 84(4), 1131-1144.

Luisi, P.L., et al., "Reverse Micelles as Hosts for Proteins and Small Molecules," Biochimica et Biophysica Acta, 947 (1988) 209-246.

Thompson, K.F., et al., "Conformation of a Peptide Solubilizate in a Reversed Micelle Water Pool," J. Am. Chem. Soc., 1984, 106, 3648-3652.

Kale, N.J., et al. "Studies on Microemulsions Using Brij 96 as Surfactant and Glycerin, Ethylene Glycol and Propylene Glycol as Cosurfactants," International Journal of Pharamceutics, 57 (1989) 87-93.

(List continued on next page.)

Primary Examiner—Carlos A. Azpuru
Attorney, Agent, or Firm—Woodcock Washburn Kurtz Mackiewicz & Norris, LLP

[57] ABSTRACT

There is provided a stable transparent multi-component composition useful for the delivery of water soluble active agents to animals. The compositions are formulated with a mixture of an oil phase, an aqueous phase, and a surfactant system, along with the active agent to be delivered to the animal. The compositions are specially formulated to be compatible with capsules such as gelatin and starch capsules. The aqueous phase of the compositions contains a substantial amount of polyethylene glycol and can optionally also contain a plasticizer. Preferred active agents are proteinaceous materials.

45 Claims, 5 Drawing Sheets

OTHER PUBLICATIONS

Gulik–Krzywicki, T., et al. "An Electron Microscopy Study of the L2–Phase (Microemulsion) in a Ternary System: Triglyceride /Monoglyceride/Water," Chemistry and Physics of Lipids, 35 (1984) 127–132.

Pilman, E. et al, "Inverse Micellar Phases in Ternary Systems of the Polar Lipids/Fat/Water and Protein Emulsification of such Phases to W/O/W–Microemulsion–Emulsions," J. Dispersion Science and Technology, 1(3), 267–281 (1990).

Fiedler, H.P., "Index of Auxiliary Substances", Pharm. Ind. 51: 1446–1449 (12) 1989.

Engstrom, L., "Aggregation and Structural Changes in the L2–Phase in the System Water/Soybean Oil/Sunflower Oil Monoglycerides," J. Dispersion Science and Technology, 11(5), 479–489 (1990).

Friberg, S., et al., "Phase Equilibria and Their Influence on the Properties of Emulsions," Jounral of the American Oil Chemists' Society vol. 47, pp. 150–152 (1970).

Engstrom, S., et al, "Enzyme Stabilization in Composite Cubic Phases," Annals New York Academy of Sciences, vol. 613, pp. 429–430.

Larsson, K., "Emulsions of Reversed Micellar Phases and Aqueous Dispersions of Cubic Phases of Lipids,", American Chemical Society, 1991, pp. 45–50.

Kemken, J., et al., "Influence of Supersaturation on the Pharma–codynamic Effect of Bupranalol After Dermal Administration Using Microemulsions as Vehicle," Pharmaceutical Research, vol. 9, No. 4, 1992 pp. 554–558.

Muller, B.W., et al., "Investigation of So–called Microemulsion Systems, Part 1," Pharm. Ind. 50, No. 11 (1988).

Muller, B.W., et al., "Investigation of So–called Microemulsions, Part 2" Pharm. Ind. 50, No. 11 (1988).

Engstrom, S., "Cubic Phases as Drug Delivery Systems", Am. Chem. Soc., Div. Polym. Chem., vol. 31 (2), pp. 157–158.

Encyclopedia of Chemical Technology, Third Edition, vol. 8, Diuretics to Emulsions, pp. 908–929.

Charman, S.A., et al. "Self–Emulsifying Drug Delivery Systems: Formulation and Bipharmaceutic Evaluation of an Investigational Lipophilic Compound," Pharmaceutical Research, vol. 9, No. 1, 1992 pp. 87–93.

Ritschel, W.A., "Microemulsions for Improved Peptide Absorption from the Gastrointestinal Tract," Meth Fun Exp Clin Pharmaco 1991 pp. 206–220.

Ganguly, R., "Active and Passive Immunization," Fundamentals of Immunology and Allergy, 1987 pp. 243–258.

Overkamp, D., et al., "Production of Polyclonal Antibodies in Ascitic Fluid of Mice: Technique and Applications," Jounral of Immunoassay, 9(1), 51–68 (1988).

Pouton, C.W., "A study of Self–Emulsifying Oil/Surfactant Mixtures," Dept. of Pharmacy, Chelsea College, University of London, Jan. 1982, pp. 1–252.

"Oral Delivery of a Resin Inhibitor Compound Using Emulsion Formulations," Pharmaceutical Research, vol. 9, No. 7, 1992.

Leon Lachman, et al., "The Theory an Practice of Industrial Pharmacy," Third Edition, 1986, pp. 374–408.

Capsugel, Divisionof Warner–Lambert Company, "General Specifications for Capsugel Hard Gelatin Capsules," Jun. 1987—USA and Canada, pp. 1–10.

TRANSPARENT LIQUID FOR ENCAPSULATED DRUG DELIVERY

This is a continuation-in-part of application Ser. No. 08/153,846 filed Nov. 17, 1993, now abandoned, which is incorporated herein in its entirety.

FIELD OF INVENTION

This invention relates to compositions useful in the delivery of biologically active agents, and methods of making and using the same. More particularly, it relates to certain unique formulations advantageously formulated to enhance delivery of such biologically active agents as drugs, proteins, and polypeptides, including therapeutically-active ones used as medicaments, in capsules designed primarily for oral administration.

BACKGROUND OF THE INVENTION

There is a continuing need for new and improved delivery systems for biologically active materials. Many of the therapeutic agents emerging from the biotechnology revolution, as well as some older drugs such as insulin and calcitonin, consist of small and large molecule proteins. These drugs must now be injected into the patient because they are unable to survive the digestive process and do not readily pass through the mucosal lining of the gastrointestinal tract and enter the bloodstream. A new drug delivery system that would enable proteins to enter the bloodstream through, for example, the lining of the digestive system would be of great benefit.

Improved drug delivery systems could also provide much improved convenience for patients. For example, calcitonin is a generic peptide hormone used for treatment of osteoporosis and other diseases involving bone loss. Osteoporosis affects 24 million Americans, including ⅔ of the women past menopause. Currently, most calcitonin is delivered by injection. Calcitonin treatment for osteoporosis requires long-term administration with low but frequent doses of the drug. An oral or suppository formulation of calcitonin would offer great advantages to patients undergoing such treatments.

Recently, thermodynamically stable compositions, such as microemulsions, micelles, and liposomes, have been used in an attempt to formulate oral drug delivery systems for proteinaceous materials. Microemulsions are known in the art as thermodynamically stable compositions of an oil, surfactant, and aqueous component which when admixed form a stable, transparent solution having a particle size of below about 200 nm and generally greater than about 5–10 nm. The microemulsions are stable in that they do not break upon standing into normal emulsions, as do emulsions made to have particle sizes below about 200 nm by the use of high shear mixing devices. Microemulsions are further described by *Science*, Kahlweit, 248, 617–621 (1988) and in Bhargava et al., *Pharm. Tech.*, 46–53 (March 1987), both of which are incorporated herein in their entirety by reference.

Water-in-oil (w/o) microemulsions are those microemulsions in which the aqueous phase is the internal phase. The w/o microemulsions can be determined by such tests as dye solubility and conductivity analysis. The w/o microemulsions generally will not initially disperse a water soluble dye. The w/o microemulsions also have a low conductivity of electricity.

Micellar solutions are in some respects similar to microemulsions, however they generally have a smaller particle size. The surfactants molecules assemble through cooperative association in the water to form aggregates called micelles. These micelles can solubilize an oil component, but generally not to the extent of a microemulsion. The term "swollen micelles" is sometimes used to refer to micellar solutions containing an oil component.

The aim of such compositions is to solubilize the proteinaceous material in an aqeuous component and to provide for the storage of the proteinaceous material while maintaining the bioavailability of the material.

Various active agents, especially proteins and peptides, must be administered to the intestinal region for proper uptake of the agent by the body. The bioavailability of these drug agents is commonly decreased upon exposure of the drug to conditions in the stomach. Therefore, the drug delivery composition is generally administered in an enterically coated capsule. Problems arise in formulating a drug delivery composition that can maintain the bioavailability of the drug within the confines of such a capsule and which can also enhance the delivery of the drug upon administration. Typically, the chemical compositions of the drug delivery composition and the capsule are thermodynamically incompatible in that mass transfer of hydrophilic materials occurs which disrupts the structural integrity of the capsule and the stability of the composition.

Water-in-oil microemulsion formulations for the delivery of biologically active materials including proteins and peptides are shown in commonly assigned co-pending application Ser. No. 07/885,202, which is herein incorporated by reference in its entirety. The formulation of the microemulsion systems into capsules, and preferably enterically coated capsules, is shown for the delivery of the active agent to the/intestines. However, it has been found that in certain embodiments, mass transfer can occur between the aqueous phase of the microemulsions and the capsule which can lead to the degradation of the capsule and microemulsion composition.

A composition that contains agents stated to form a microemulsion in the gastrointestinal tract is disclosed in U.S. Pat. No. 5,206,219 to Desai. The compositions of Desai require the presence of cholesterol and a phospholipid. The water content of the compositions is maintained below 5% w/w and such polyol co-solvents as propylene glycol and polyethylene glycol are included as hydrophilic materials. The requirement of the presence of the cholesterol and phospholipid unduly restricts the formulation of a drug delivery system.

A need therefore exists to formulate a drug delivery composition, useful for the delivery of such active agents as proteins and peptides, that can be prepared and stored within a capsule while maintaining the stability of the system and the bioavailability of the active agent.

SUMMARY OF THE INVENTION

Drug delivery compositions are provided herein which contain an oil phase, an aqueous phase, a surfactant or mixture thereof, and a therapuetic, preferably proteinaceous, active agent. The drug delivery composition is a transparent composition and is thermodynamically stable. Such a drug delivery composition is suitable for storage and administration of the active agent, preferably by an oral route.

The drug delivery compositions are specifically formulated to be compatible with capsules. Thus, the compositions exhibit excellent storage stability in a capsule form. The compositions contain an aqueous phase containing a major amount of polyethylene glycol and a minor amount of water either alone or in admixture with a plasticizer. Such formulations are vastly superior in the capsule form to corresponding w/o microemulsion formulations having major amounts of water in the aqueous phase.

The drug delivery compositions are distinguished from those oral multi-component drug delivery compositions which are formulated to form a microemulsion in situ in the intestine in that they do not require the presence of a phospholipid in conjunction with a cholesterol component.

BRIEF DESCRIPTION OF THE DRAWINGS

Compositions of the present invention are graphically depicted in FIGS. 1–5. Apex A represents 100 wt. % of the aqueous phase, apex B represents 100 wt. % of the oil phase, and apex C represents 100 wt. % of the surfactant and permeation enhancers. The shaded area represents compositions that produce transparent solutions. All parts are on a weight basis.

DESCRIPTION OF THE INVENTION

Figure 1:
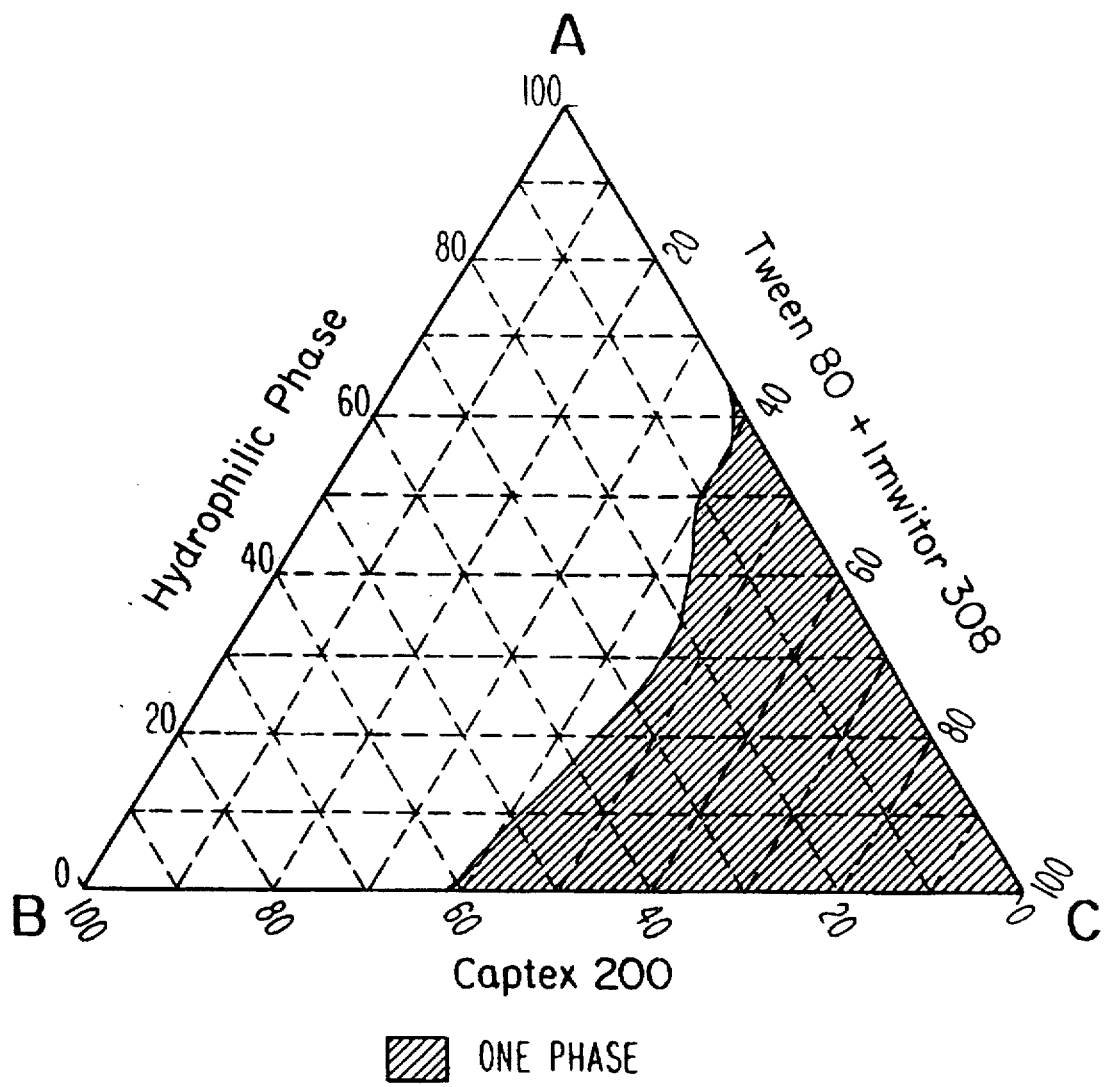
FIG. 1 is a phase diagram wherein the aqueous phase constituted 8.6 parts PEG 600, 1 part water, and 0.4 parts sorbitol. The oil phase constituted Captex 200 and the surfactant phase constituted 6 parts Imwitor 308 and 4 parts Tween 80.

Drug delivery compositions are described herein which contain an oil or lipid (hydrophobic) phase, an aqueous (hydrophilic) phase, and a surfactant or mixture of surfactants, and an active agent, preferably biologically active, more preferably a therapeutic, proteinaceous active agent. The drug delivery compositions are optimized for use in conjunction with capsules for oral, rectal, and vaginal, preferably oral and rectal, and more preferably oral, administration. However, the compositions of this invention can be administered by any method such as parentoral, enteral, and any other mucousal means and without a capsule container.

The present invention provides for the transparent solutions with and without the active agent. The compositions formulated without the active agent are generally referred to as delivery compositions, and with the active agent is generally referred to as drug delivery compositions. The delivery compositions have various uses, but are primarily useful as pharmaceutical compositions into which an active agent, such as those defined in this invention, can be incorporated.

The delivery compositions have been designed to be compatible with a capsule container by formulating the components of the aqueous phase to contain a major amount of polyethylene glycol (PEG) and a minor amount of water or saline. The ratio of PEG to water is altered in accordance with the composition of the capsule material to optimize the stability between the delivery composition and the capsule composition. In such a way, the mass transfer between the capsule and the delivery composition is decreased resulting in a more stable overall formulation.

The present delivery compositions are described as multi-component systems. The delivery compositions of the present invention are preferably transparent, thermodynamically stable solutions resembling swollen micelles and w/o microemulsions, however the particle size of the present compositions may not fall within the ranges commonly understood to encompass micelles and microemulsions. Generally, the particle sizes for the inventive compositions are below about 15 nm, preferably below about 10 nm, and more preferably below about 5 nm, and thus the compositions can also be referred to as solutions.

The delivery compositions can be formulated with any of the following ranges of oils, aqueous phase components, and surfactants. The compositions can be prepared without the need for a mixture of a phospholipid and cholesterol component.

The oil phase of the delivery compositions contains at least one oil component. The oil component is generally any such known oil accepted in the food or pharmaceutical industry. The oil, or mixtures thereof, may be liquid at room temperature, although in some cases, mild heating of a solid oil to form a liquid is acceptable. Heating of an oil that is solid at room temperature is desirable for formulations intended as suppositories, creams, salves, and in some cases as oral capsules.

Illustrations of suitable oils for purposes of this invention include triesters of glycerol having from about 9 to 83, preferably 21–60, and more preferably 21–45 carbon atoms. The triglycerides are further defined as short chain triglycerides having 9–15 carbon atoms, medium chain triglycerides having 21–45 carbon atoms, and long chain triglycerides having above 45 carbon atoms. Medium chain triglycerides are preferred. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Commercially available triglyceride oils, both natural and chemically-synthesized, are available from Karlshamns Lipid Specialties, U.S.A. as the Captex® series, and from Huls America Inc. as the Miglyol series.

Other suitable oils include diesters of propylene glycol having from about 7 to 55, preferably 15–40 carbon atoms, more preferably propylene glycol esters of capric and caprilic acids, and mixtures thereof, having from 19 to 23 carbon atoms. The diesters of propylene glycols are further defined as short chain having from 7–11 carbon atoms, medium chain having from 15–31 carbon atoms, and long chain having above 31 carbon atoms. Preferred propylene glycol diesters are the medium chain oils. Diesters of propylene glycols include propylene glycol esters of capric acid, caprylic acid, and mixtures thereof such as Captex® 200, and Captex® 800 (Karlshamns Lipid Specialities, Columbus, Ohio) and other ester groups as described above for glycerol.

The oils can be of natural or synthetic origin and can contain fatty acids of different lengths within their structure. Other lipophilic oil components can also be used in the oil phase such as fish oil products and mineral oil products.

Other lipophilic materials that function as an oil phase are also encompassed by this invention. Such oil components are preferably food or pharmaceutical grade quality.

The oil phase is present in the delivery compositions from about 1 to about 80, preferably from about 5 to about 70, and more preferably from 8 to 50 weight percent. This weight percent basis is based on the total weight of the components which make up the transparent delivery composition, that is, the oil phase components, the aqueous phase components, and the surfactant components, without the active agent or optional additives such as the antioxidants, preservatives, etc.

The delivery compositions of the present invention are created by the interplay between the surfactant or mixture of surfactants (the "surfactant component") and the oil and aqueous phase components. The surfactant component can be described by its hydrophilic-lipophilic balance (HLB) which is an empirical quantity, on an arbitrary scale, which is a measure of the polarity of a surfactant or mixture of surfactants. See P. Becher et al., "Nonionic Surfactant, Physical Chemistry," Marcel Dekker, New York (1987), pages 439–456. It is a widely known and used term.

The delivery compositions of the present invention can be prepared with either a single surfactant or a mixture of surfactants. The final HLB of the composition is generally at least about 5, preferably from about 5 to about 15. The compositions are preferably prepared with a mixture of surfactants to allow for versatility, greater stabity, and enhanced drug adsorption. The surfactant component generally contains at least one low HLB surfactant having an HLB below 10, preferably below 8 and at least one high HLB surfactant having an HLB above 10, preferably above 12.

The surfactant component is present in the delivery compositions in an amount of from about 3 to about 98, preferably from about 10 to about 80, more preferably from about 15 to about 75, weight percent.

Surfactants which may be employed in the delivery compositions include both ionic agents, i.e., cationic, anionic or zwitterionic, and non-ionic agents, or mixtures thereof. Examples of cationic surfactants include cetyldimethylethylammonium bromide, cetylpyridinium chloride and other salts of these surfactants. Short chain monohydroxyl alcohols, such as $C_1$ to $C_6$ alcohols, are preferably not employed as surfactants in these systems due to toxicity factors, thus the compositions are substantially free of such short chain monohydroxyl alcohols. Various surfactants also have permeation enhancement properties.

Examples of anionic surfactants include $C_{8-32}$ fatty acids and salts thereof, preferably $C_{8-12}$, more preferably $C_8$; cholic acid and derivatives thereof such as deoxycholate, and its salts, ursodeoxycholic acid, and taurocholic acid; $C_{8-56}$ diesters of tartaric acid; phospholipids such as phosphatidic acid and phosphatidyl serine; $C_{5-29}$ monoesters of lactic acid; $C_{8-20}$ sulfonates, including alkyl-, olefin-, and alkylaryl derivatives; tridecyl- and dodecylbenzene sulfonic acids; and $C_{5-33}$ sarcosine and betaine derivatives.

Zwitterionics include such phospholipids as lecithin, phosphatidylethanolamine, and sphingomyelins. The phospholipids are particularly preferred for use as both the low and high HLB surfactants.

Among the non-ionic surfactants which may be employed are ethoxylated castor oil; $C_{5-29}$ mono-glycerides and ethoxylated derivatives thereof; $C_{15-60}$ diglycerides and polyoxyethylene derivatives thereof having 1 to 90 POE groups; $C_{10-40}$ esters (10–40 carbon atoms in the alcohol) of long chain fatty acids (fatty acids having 16 carbon atoms and above); $C_{10-40}$ alcohols; sterols such as cholesterol, ergosterol, and $C_{2-24}$ esters thereof; $C_{8-96}$ ethoxylated fatty esters; $C_{14-130}$ sucrose fatty esters; and $C_{20-130}$ sorbitol and sorbitan monoesters, diesters, and triesters, and polyoxyethylene (POE) derivatives thereof having 1 to 90 POE groups, e.g., polyoxyethylene sorbitan monooleate, sorbitol hexaoleate POE (50).

Preferred low HLB surfactants include $C_9$ to $C_{13}$ monoglycerides, $C_{19}$ to $C_{25}$ diglycerides of mono and poly unsaturated fatty acids, $C_{15}$ to $C_{23}$ diglycerides, and $C_{35}$ to $C_{47}$ diglycerides of mono and poly unsaturated fatty acids. Especially preferred low HLB surfactants are those containing at least about 80 percent by weight, preferably at least about 90 percent by weight, and more preferably at least about 95 percent by weight, of a monoglyceride or diglyceride containing $C_6$, $C_7$, $C_8$, $C_9$, or $C_{10}$ fatty acid functionalities, or mixtures thereof, preferably a $C_9$, $C_{11}$, or $C_{13}$ monoglyceride or mixtures thereof, and more preferably a $C_{11}$ or $C_{13}$ monoglyceride or mixtures thereof. Commercial examples of these surfactants include Imwitor 308, manufactured by Huls America, Inc., having about 80–90% wt. $C_{11}$ monoglycerides; and Glycerol Monocaprylin, manufactured by Sigma Chemicals as 1-monooctanoyl-rac-glycerol having about 99% wt. $C_{11}$ monoglycerides, and Glycerol Monocaprate, manufactured as 1-monodecanoyl-rac-glycerol by Sigma Chemicals, having about 99% wt. $C_{13}$ monoglycerides. In certain preferred embodiments, the low HLB surfactant, or mixture of low HLB surfactants, will be only the above recited monoglycerides having a purity of at least about 80 weight percent.

Preferred high HLB surfactants include the sorbitan surfactants, preferably those having an HLB of from about 13 to about 17. Such surfactants include POE (20) sorbitan monooleate, monostearate, monopalmitate, and monolaurate sold commercially as the Tween 80, 60, 40, and 20, respectively by ICI Inc., and POE (4) sorbitan monolaurate sold commercially as Tween 21 by ICI. Also preferred are ethoxylated castor oil surfactants, preferably those having an HLB of from about 12 to about 20, such as Cremophor EL, RH-40, and RH-60 and the Pluronic F-series sold by BASF Inc. Potassium oleate is also preferred as a high HLB surfactant.

The low HLB surfactant is preferably present in the delivery composition in an amount of from about 1 to about 40, preferably from about 5 to about 30, more preferably from about 10 to about 30 weight percent, and in certain preferred embodiments from 20 to 30 weight percent. The high HLB surfactant is present in the delivery composition in an amount of from about 2 to about 60, preferably from about 5 to about 50, and more preferably from about 10 to about 40 weight percent.

The active agent is solubilized in water within the drug delivery compositions. The water, or saline solution, is present in the delivery composition in an amount of from about 0.5 to about 15, preferably from about 1 to about 10, more preferably from about 2 to about 8, weight percent, however in some high water systems, the water is present in an amount of from greater than 5 to about 15, preferably from 8 to about 15, weight percent. This low level of water allows for solubilization of the active agent and also provides compatibility between the delivery composition and the capsule composition.

Polyethylene glycol (PEG) is incorporated into the delivery compositions to promote compatibilty with the capsule composition. The capsules useful with the present invention include hard and soft gelatin capsules and starch capsules. The hard and soft gelatin capsules are made from gelatin blends as fully discussed in *The Theory and Practice of Industrial Pharmacy*, Lachman et al., Lea & Febiger, p. 374–408 (3d Ed. 1986), which is hereby incorporated by reference in its entirety. The gelatin is a heterogeneous product derived by irreversible hydrolyric extraction of treated animal collagen from such sources as animal bones, hide portions, and frozen pork skin. The gelatin can be blended with plasticizers, such as glycerin USP and sorbitol USP, and water. The ratio of glycerin to gelatin is from about 0.4:1 to about 0.8:1 for the hard and soft gelatin capsules, respectively. The moisture content for hard gelatin capsules ranges from about 10–16% and from about 5–12% for soft gelatin capsules at a relative humidity of about 25% at about 22° C. The gelatin capsules can also contain such additives as preservatives, colorants, flavorants, etc. Commercially available gelatin capsules are these made by CAPSUGEL, a division of Warner-Lambert Co., which are available in a general capsule size range of from #5 to #000 having volumes of from about 0.1–1.4 ml.

The PEG component is present in the delivery compositions in an amount of from about 2 to about 60, preferably from about 5 to about 55, and more preferably from about 15 to about 55, weight percent. The PEG component typically has a weight average molecular weight of from about 200 to about 1200 and commercially available PEG materials include PEG 200, PEG 300, PEG 400, PEG 540, PEG 600, PEG 800, and PEG 1000 all commercially available from, for example, Union Carbide Corp. in both food or pharmaceutical grades. The PEG component also functions as a solvent for the low HLB surfactants and permeation enhancers, and as a stabilizer for the active agent, especially proteins and peptides.

A plasticizer can also be incorporated into the delivery compositions to prevent mass transfer between the capsule and the delivery compositions. Such plasticizers include sorbitol, mannitol, glycerin, propylene glycol, and sugar compounds such as sucrose, glucose, fructose, lactose and similar sugar compounds. The plasticizer is present in an amount of from about 0.5 to about 10, preferably from about 0.5 to about 8, and more preferably from about 1 to about 5, weight percent of the delivery composition. Propylene glycol is preferably not employed as a plasticizer in the compositions of the present invention for their use as encapsulated products since it is believed that propylene glycol causes capsule instability during storage. Thus, the compositions for encapsulated use can be prepared provided that the plasticizer is not propylene glycol in certain preferred embodiments.

In one embodiment of the present invention, the delivery compositions can be described as having an aqueous phase, that is, components that are highly soluble with the water and not considered to be high HLB surfactants. The aqueous phase contains primarily the water, PEG component, and plasticizer component. This aqueous phase is present in the delivery composition in an amount of from about 1 to about 70, preferably from about 5 to about 60, and more preferably from about 8 to about 55, weight percent. The aqueous phase contains a major amount of the PEG component and a minor amount of water or saline, and plasticizer. The aqeuous phase contains from about 60 to about 95, preferably from about 70 to about 90, and more preferably from about 75 to about 90 weight percent of the PEG component. The water, or saline, content of the aqueous phase is from about 2 to about 30, preferably from about 5 to about 15, more preferably from about 7 to about 13, weight percent. The ratio of the PEG component to the water in the compositions is generally at least about 2:1, preferably from about 2:1 to about 99:1, more preferably from about 4:1 to about 95:5, and even more preferably from about 5:1 to about 95:5. The plasticizer is present in an amount of from about 1 to about 15, preferably from about 2 to about 12, and more preferably from about 3 to about 9, weight percent of the aqueous phase.

The active agent to be incorporated into the drug delivery compositions is preferably water-soluble. The water-soluble active agent can be any biologically active, preferably therapeutic material, particularly water-soluble proteins, peptides and other pharmaceutically-active compounds, i.e., drugs or medicaments, and compounds which may have use as diagnostic agents. Vitamins and other food supplements which are not commonly defined as being "therapeutic" are not within the definition of the active agent.

Therapeutic agents suitable for use in these systems are characterized by the following general properties. The agents are polar, water soluble compounds with an octanol-:water partition coefficient less than about 0.1, preferably less than 0.05 and more preferably less than about 0.001 when the aqueous phase has a pH of from about 5.5 to about 8.5, the pH range of the mammalian intestinal tract. The agents have molecular weights greater than about 200, preferably greater than 300 and more preferably greater than 400. Suitable agents are also characterized by poor absorption through the GI tract with oral bioavailablilities (compared to i.p. availabilities) less than about 50%, preferably less than about 35% and more preferably less than about 20% when administered at therapeutic dosage levels.

By "therapeutic" is meant an amount of the agent that produces the usual and desired pharmacological or physiological response to that agent elicited when it is administered by parenteral routes. The amount of active material to be administered to be "therapeutic" will be easily determined by those skilled in the art based upon concentration of dosage and the repetition of the dosage.

Chemical classes of suitable therapeutic agents include the water soluble proteins or peptides. One group of agents are water soluble peptides having a molecular weight from about 300 to about 2,000 (all molecular weights herein are weight average) and containing at least one and preferably two or more peptide bonds. A second group of agents are water soluble polypeptides from about 2,000 to about 10,000 weight average molecular weight having at least three and preferably five or more peptide bonds. A third group of agents are water soluble proteins having molecular weights greater than 10,000 and containing at least six and preferably ten or more peptide bonds.

These active agents are admixed with the delivery compositions to form the drug delivery compositions. The general amount of active agent is up to about 500 mg per gram of the drug delivery composition and in most cases from about 0.5–300 mg/g drug delivery composition. The amount of active agent included in the drug delivery composition may be varied considerably, depending upon its solubility and activity, the use for which it is intended, the amount of emulsion to be employed, and the like.

Suitable therapeutic peptides of molecular weight 300 to 2,000 having 3 to 10 amino acid moieties include: fibrinogen receptor antagonist peptides, RGD containing peptides, which are tetrapeptides of average molecular weight of about 600, having the amino acids arginine-glycine-aspartic acid, in that order, as part of their sequence with the fourth position of the tetrapeptide variable. Such peptides are highly potent platelet aggregation inhibitors active at plasma concentrations as low as 1 pmol/mL. A preferred fibrinogen antagonist is the peptide cyclo(S,S)-N$^\alpha$-acetyl-Cys-(N$^\alpha$-methyl)Arg-Gly-Asp-Pen-NH$_2$ (SEQ ID NO:1) prepared by the method of Ali et al., published application EP 0 341 915 whose disclosure is herein incorporated by reference in its entirety. Also preferred is the peptide cyclo(S,S)-(2-mercapto)benzoyl-(N$^\alpha$-methyl)Arg-Gly-Asp-(2-mercapto) phenylamide which may be prepared by the method disclosed in published EPO 0423212, Application No. 90311537.6 whose disclosure is herein incorporated by reference in its entirety.

RGD-containing peptides and peptide-like molecules are generally present in amounts ranging from about 10 mg to about 500 mg per gram of the drug delivery composition depending on the solubility and therapeutic potency of the compound.

Other fibrinogen antagonists useful in the present invention are those peptides disclosed in Pierschbacher et al., WO 89/05150 (US/88/04403); Marguerie, EP 0 275 748; Adams et al., U.S. Pat. No. 4,857,508; Zimmerman et al., U.S. Pat. No. 4,683,291; Nutt et al., EP 0 410 537; Nutt et al., EP 0 410 539; Nutt et al, EP 0 410 540; Nutt et al., EP 0 410 541; Nutt et al., EP 0 410 767; Nutt et al., EP 0 410 833; Nutt et al., EP 0 422 937; Nutt et al., EP 0 422 938; Alig et al., EP 0 372 486 Ohba et al., WO 90/02751 (PCT/JP89/00926); Klein et al., U.S. Pat. No. 4,952,562; Scarborough et al., WO 90/15620 (PCT/US90/03417); Ali et al., PCT US 90/06514, filed Nov. 2, 1990; peptide like compounds as disclosed in Alig et al., EP 0 381 033; and Alig et al., EP 0 384 362, the disclosures of all of these being incorporated herein in their entireties by reference; and the cyclic RGD peptides:

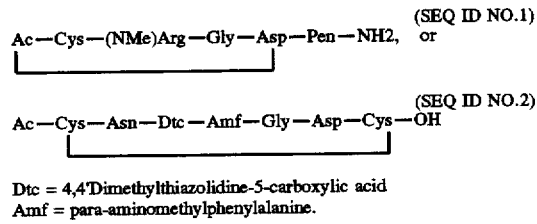

Dtc = 4,4'Dimethylthiazolidine-5-carboxylic acid
Amf = para-aminomethylphenylalanine.

Enkephalins and analogues are other examples of peptides that may be usefully incorporated into these formulations. These peptides have analgesic properties and are based on the structures of the two naturally occurring enkephalins, [Leu$^5$]-enkephalin, a pentapeptide with the sequence, H$_2$N-Tyr-Gly-Gly-Phe-Leu-OH (SEQ ID NO. 3, MW=556), and [Met$^5$]-enkephalin, with a sequence, H$_2$N-Tyr-Gly-Gly-Phe-Met-OH (SEQ ID NO.4, MW=574). Examples of analogues include peptides in which one or two of the natural L-stereoisomers of the amino acid residues is replaced by the corresponding D-stereoisomer, such as [D-Ala$^2$, Leu$^5$]-enkephalin (MW=570) or [D-Ala$^2$, D-Met$^5$]-enkephalin (MW=588). Also useful are analogues containing one or more non-amino acid or chemically modifier amino acid moieties, such as [D-Pen$^{2,5}$, PCl-Phe$^4$]-enkephalin (MW=680) which interacts selectively with the delta-class of opioid receptor (see Vaughn, L. K., et.al, Life Sciences, 45, 1001, 1989, incorporated herein in its entirety by reference).

Another useful class of peptides are hexapeptides related to growth hormone releasing peptide (GHRP). Specific examples include the peptide His-D-Trp-Ala-Trp-D-Phe-Lys-NH$_2$ and related homologues and analogues. Also useful is the analogue Ala-His-D-βNal-Ala-Trp-D-Phe-Lys-NH$_2$, where D-Trp is replaced by D-[β-naphthyl]-alanine (C. Y. Bowers, J. Pediatr. Endocrinol., 6, 21, 1993, incorporated herein in its entirety by reference). Growth hormone releasing peptides are disclosed, for instance, in Momany, U.S. Pat. No. 4,411,890; Momany, U.S. Pat. No. 4,410,513; Momany, U.S. Pat. No. 4,410,512; Momany, U.S. Pat. No. 4,228,158; Momany, U.S. Pat. No. 4,228,157; Momany U.S. Pat. No. 4,228,156; Momany, U.S. Pat. No. 4,228,155; Momany, U.S. Pat. No. 4,226,857; Momany U.S. Pat. No. 4,224,316, Momany U.S. Pat. No. 4,223,021; Momany, U.S. Pat. No. 4,223,020; Momany, U.S. Pat. No. 4,223,019; Bowers et al., U.S. Pat. No. 4,880,778; Bowers et al., U.S. Pat. No. 4,880,777; Bowers et al., U.S. Pat. No. 4,839,344; Bowers et al., U.S. Pat. No. WO 89/10933 (PCT/US89/01829); Bowers et al., EP-A 398 961, Bowers et al. EP-A 400 051, all of which are fully incorporated herein by reference. These compounds are useful for accelerating the growth of humans and animals.

Antagonists of GHRP are useful in clinical situations where abnormally accelerated growth or excessive plasma levels of growth hormone are encountered. Examples of a specific GHRP antagonist include the hexapeptide His-D-Trp-D-Lys-Trp-D-Phe-Lys-NH$_2$. Both agonists and antagonists of GHRP are usefully present in the range of 0.001 to 100 mg per gram of drug composition, depending on their potency.

Nonapeptidyl vasopressin V$_1$ and V$_2$ receptor agonists and antagonists are used clinically to treat conditions of excessive urinary output and blood clotting factor VIII deficiency. Particularly useful agents include arginine vasopressin (AVP), lysine vasopressin (LVP) and desmopressin (dDAVP), molecular weights 1084, 1056 and 1069 respectively. Desmopressin is particularly preferred for incorporation into an oral dosage form, because it has a longer plasma half-life and lacks the pressor (vasoconstricting) activities of AVP or LVP. Desmopressin has been utilized in an oral dosage form, but the oral bioavailability is poor, only 0.1 to 0.2% (A. Fjellestad-Paulsen, O. Paulsen, L. d'Agay-Abensour, S. Lundin and P. Czernichow, Regulatory Peptides 43, 303–307, 1993, incorporated herein in its entirety by reference). AVP, LVP or dDAVP are usefully incorporated into the formulation at levels ranging from about 0.01 to 10.0 mg per gram of drug composition. Other V$_1$ or V$_2$ vasoproessin receptor agonists or antagonists which are homologues or analogues of the above compounds may be incorporated at higher levels, but generally less than 200 mg per gram of drug composition, depending on their therapeutic potency and solubility.

Yet another class of useful peptides include luteinizing hormone-releasing hormone (LH-RH) and its analogues. These peptides contain about 10 natural or synthetical produced amino acid residues and have molecular weights ranging from about 1,000 to about 1600. Suitable examples include LH-RH itself, with a sequence of pGlu-His-Trp-Ser-Tyr-Gly-Leu-Arg-Pro-Gly-NH$_2$ (SEQ ID NO.5, MW=1182) where pGlu stands for a pyroglutamic acid residue and the C-terminus of the peptide is amidated (—NH$_2$); the LH-RH agonist analogue, Des-Gly$^{10}$, D-Trp$^6$, Pro$^9$]-LH-RH, ethyl amide (MW=1283); and the LH-RH antagonist, Antide (MW=1592) which has a sequence N-acetyl-D-βNal-p-Cl-D-Phe-3-Pyridyl-D-Ala-Ser-N-ε-Nicotinoyl-Lys-N-ε-Nicotinoyl-D-Lys-Leu-N-ε-Isopropyl-Lys-Pro-D-Ala-NH$_2$. Leuprolide, 5-OxoPro-His-Trp-Ser-Tyr-D-Leu-Leu-Arg-pro-NHC$_2$H$_5$ (MW=1210), is another LH-RH analogue and is useful for the treatment of prostatic carcinoma.

Melanocyte stimulating hormones (MSH's) and analogues, having molecular weights ranging from about 800 to about 3000, may also be usefully incorporated into these formulations. Particularly preferred are analogues displaying prolonged circulatory half-lives and/or increased resistance to proteolytic degradation.

Peptidyl proteinase inhibitors are another category of peptides and peptide analogues that may be usefully incorporated into the drug composition. Particularly preferred are: inhibitors of metalloproteinases, such as collagenase and elastase, which are useful in treating certain metastatic cancers and certain inflammatory diseases, such as arthritis; inhibitors of proteases coded on viral genomes, such as the HIV-1 and HIV-2 viral proteases; inhibitors of angiotensin converting enzyme (ACE inhibitors) or of renin, useful in the treatment of hypertension; and inhibitors of blood clotting cascades proteases, such as thrombin inhibitors, useful for treating thrombosis. Also useful as antithromobics are peptides and polypeptide fragments of the leech protein hirudin, as well as analogues of these fragments and hirudin itself.

Calcitonins, such as those set forth in U.S. Pat. No. 5,002,771 which is incorporated herein in its entirety, are a set of therapeutic polypeptides useful for treating hypercalcemia and bone loss. Preferred calcitonins for incorporation into the formulation are salmon, eel and haman calcitonins. Salmon calcitonin and eel calcitonin are most preferred because of their higher potency and more favorable pharmacokinetic profile. Human calcitonin is preferred in those patients where adverse reactions or insensitivity to the others is known or suspected. Synthetic salmon, eel or human calcitonins have the same amino acid sequence as their naturally occurring counterparts, but may, in some cases, be truncated or chemically altered versions of the natural molecule, as for example is the case for carbacalcitonin which is [Des-Cys$^1$, Asu$^7$]-eel calcitonin. Their molecular weights range from about 3300 to 3500.

Other polypeptide regulators of calcium metabolism which could be usefully included in the formulation include the 84 amino acid residue polypeptides human or bovine parathyroid hormone (PTH) with molecular weights of 9425 and 9511, respectively, and truncated versions and biologically active fragments thereof having 14 to 83 amino acid residues and molecular weights from 1400 to 9950. Also useful in this category are PTH-related peptides, such as the human hypercalcemia of malignancy peptide which a has 86 amino acid residues and a molecular weight of 9903. Biologically active fragments of this molecule having 14 to 85 amino acid residues and molecular weights from about 1400 to about 9950 may also be usefully included in the formulation, as well as polypeptide analogues of such fragments having agonist or antagonist activities.

Antrial natriuretic peptides (ANP's) and their analogues are polypeptides useful for treatment of hypertension. Particularly preferred for use in these formulations are human ANP's and their analogues with molecular weights of from about 1000 to about 4000. Brain natriuretic peptides are also useful for this purpose.

The insulins are another group of polypeptides which may be incorporated into the formulation. Human, bovine, porcine or ovine insulins or chemically modified derivatives thereof would be particularly preferred. This insulins are disulfide-linked, dimeric polypeptides having two distinct chains, A and B, and a molecular weight of about 6000 for the dimeric molecule.

Other useful polypeptides in this molecular weight range include amylin, insulin-like growth factors I, II and III (IGF-I, IGF-II, IGF-III) , somatomedins, epidermal growth factor (EGF), and transforming growth factor-α (TGF-α). Polypeptide analogues of these molecules may also be incorporated into the formulation.

Proteins useful for incorporation into these formulations include: human, bovine, ovine or porcine growth hormone; α-, β-, or γ-interferons; lymphokines, such as interleukins 1 to 6; growth factors, such as platelet-derived growth factor, acidic or basic fibroblast growth factor; therapeutic enzymes, such as asparaginase or superoxide dismutase; erthropoietins; and monoclonal antibodies or their antigen-binding fragments.

Further, suitable agents include water soluble complex polysaccharides having at least two and preferably three or more monosaccharide units and additionally containing one or more of the following chemical substituents: amino groups (free or acylated), carboxyl groups (free or acylated), phosphate groups (free or esterified) or sulfate groups (free or esterified).

Particularly preferred polysaccharides include heparins, useful as anticoagulants, and polysaccharide inhibitors of the mammalian cell lectins, known collectively as 'selectins', useful as anti-inflammatory agents.

Also, suitable agents include nucleosides, nucleotides and their polymers. Suitable nucleosides include 3'-azido-3'-deoxythimidine, 2',3'-dideoxy-derivatives of adenosine, cytidine, inosine, thymidine or guanosine. Suitable polynucleotides include "anti-sense" nucleotides having 3 to 30 nucleotide bases with nucleotide sequences complimentary to those coding for viral proteins or RNA's, oncogene proteins or RNA's, or inflammatory proteins or RNA's. Also useful are polynucleotides having 3 to 30 bases capable of forming triple helix structures with the DNA coding for the above.

Preferred water soluble active agents include RGD fibrinogen receptor antagonists, enkephalins, growth hormone releasing peptides and analogues, vasopressins, desmopressin, luteinizing hormone releasing hormones, melanocyte stimulating hormones and analogues, calcitonins, parathyroid hormone, PTM-related peptides, insulins, atrial natriuretic peptides and analogues, growth hormones, interferons, lymphokines, erthropoietins, interleukins, colony stimulating factors, tissue plasminogen activators, tumor necrosis factors, complex polysaccharides, and nucleosides, nucleotides and their polymers.

Drugs that can be employed in this system are water soluble drugs which are characterized by having low oral bioavailability. Examples of some of the drugs that can be employed include: anticoagulants, such as heparin or its derivatives; antimicrobials, such as penicillin G, carbenicillin, meziocillin and other poorly absorbed penicillin derivatives; cephalosporins, such as cephalothin, cefoxitin, cefotaxime and other molecules in this series normally administered by injection; antineoplastic drugs, such as fluorouracil, cytarabine, azauridine, thioguanine, vinblastine, vincristine, and bleomycin; anti-inflammatories, such as aurothioglucose and gold sodium thiomalate; and antiparasitic drugs, such as suramin and mebendazole.

The drug delivery compositions can be formulated with agents for enhancing mucosal absorption of peptides and proteins. These include bile salts such as trihydroxy bile salts, i.e. cholate, taurocholate, and glycocholate, dihydroxy bile salts, i.e. deoxycholate, taurodeoxycholate, chenodeoxycholate, and ursodeoxycholate, triketo bile salts such as dehydrocholate. Non-ionic surfactants such as polyoxyethylene ethers with alkyl chain lengths from 12–18 carbon atoms and polyoxyethylene (POE) chain lengths from 2–60, p-t-octylphenoxypolyoxyethylenes with 2–60 POE groups, nonylphenoxypolyoxyethylenes with 2–60 POE groups, polyoxyethylene sorbitan esters with 8–24 alkyl chain lengths and 4–80 POE groups, and 1-dodecylhexahydro-2H-azepin-2-one(azone, laurocapram) can be used. Anionic surfactants such as sodium dodecyl sulfate and dioctyl sodium sulfosuccinate can be used. Lysolecithins containing saturated fatty acyl chains having 8–24 carbon atoms or unsaturated fatty acyl chains having 1 to 4 double bonds and 16–24 carbon atoms can be used. Acylcarnitines, acylcholines and acylamino acids can be used, such as acylcarnitines having 12–20 carbon acyl groups and where the acyl groups have 1–4 double bonds, acylcholines such as acyl choline esters of fatty acids having 8–22 carbon atoms and 1–4 double bonds, and acylamino acids such as N-acyl amino acids and dipeptides having acyl groups with 8–24 carbon atoms and 1–4 double bonds and the amino acids having $\alpha$ or $\beta$ amino groups and a molecular weight less than 350. Additionally, mono and polyunsaturated fatty acids and their salts having 14–24 carbon atoms and 1–4 double bonds, and salicyclic acid and its sodium salt, sodium 5-methoxy-salicylate can be used.

Preferred permeation enhancers include $C_{8-18}$ fatty acids, acylcarnatine, cholic acids, and phospholipids, or combinations thereof. These function particularly well in combination with the preferred low HLB surfactant, such as the mono- and di-glycerides having from $C_{8-10}$ fatty acid functionalities. A particularly preferred combination of permeation enhancers is a mixture of $C_{11}$ monoglyceride (such as Imwitor 308), oleic acid, and phospholipids.

The stabilization of the active agent, especially proteins or peptides, is generally enhanced by altering the pH and the buffering capacity of the aqueous phase of the compositions. Such compounds as HCl and NaOH can be used to adjust the pH and such compounds as acetic acid can be used as buffers. A pH of below about 5 is typically preferred with such proteins as calcitonin, dDAVP, RGD peptides and their analogs. The PEG component itself can stabilize other proteinaceous agents such as human growth hormone.

Other components can be used in conjunction with the drug delivery compositions to inhibit or prevent the degradation of the proteinaceous active agents. Such components include protease inhibitors, enzyme inhibitors, and stabilizers as shown in U.S. Pat. No. 5,206,219 which is incorporated herein by reference. A preferred stabilizer is cyclodextrin.

In addition, there may optionally be included into the formulations such other adjuvants as antioxidants, coloring agents, oil soluble drugs and the like. Each of these components and adjuvants must be suitable for use in the subject and will usually be food grade and/or pharmaceutically-acceptable materials.

The compositions of the present invention are biologically compatible in that they are non-toxic and contain biodegradable or non-absorbable materials. By non-toxic it is meant non-toxic dependent upon the route of administration to a subject, in that the toxicity of one route may not be equivalent to that of another route.

Adjuvants, such as preservatives, coloring agents, flavors or oil-soluble drugs, e.g., steroids, if any, should be included only in those amounts which will not adversely affect the novel properties of the composition, generally in amounts of up to 20% by volume, based on the total volume of the drug delivery composition.

The delivery compositions of this invention may readily be prepared by simply mixing together with mild agitation the selected components in the desired ratios at room temperature or at slightly elevated temperatures. No high-energy mixing or application of heat is necessary, although limited use of each may be employed, if desired, to increase the rate of formation of the compositions. Moreover, the ingredients do not have to be added in any particular order other than that it is preferred for the active agent to be present in the aqueous phase as the composition is formed. Preferably, however, the surfactant should first be mixed with the oil phase, followed by the addition of the aqueous phase components in the proper ratio. It is preferred to dissolve the active agent in the water first, and then add this to the other aqueous phase components.

The delivery composition of the present invention can be formulated with a high melting oil, that is, an oil with a melting point above room temperature (22°–23° C.), preferably above about 30° C., in order to formulate a composition which is a solid at room temperature. Also, high melting surfactants such as a $C_{10-40}$ ester of a long chain fatty acid and alcohols having at least about 12 carbon atoms, wherein these surfactants have melting points above room temperature, preferably above about 30° C. Preferably, the composition will melt at body temperatures, generally between about 35°–40° C. The amount of high melting oil and the melting point of that oil can vary, but the final composition is solid at room temperatures. The solid composition can be used as a suppository transport vehicle or as an oral transport vehicle. The composition can either be formulated directly with the high melting oil, or the composition can be formulated first, after which the high melting oil is blended with the composition. Such high melting oils are well known in the art and include, for example, partially hydrogenated coconut oils, palm oils, cocobutter, hydrogenated peanut oil, and various hydrogenated vegetable oils, along with combinations thereof. Preferred oils include hydrogenated coconut and palm oils and mixtures thereof. The high molecular weight PEG components can also be used to formulate a solid composition.

The administration, especially oral adminstration, of the active agent, contained within the drug delivery composition, is preferably in the form of a capsule. The capsule is generally a starch or gelatin material. Certain active agents may be susceptible to the low pH environment of the stomach and should therefore be delivered to the higher pH environment of the intestinal system. Although such active agents are beneficially delivered in suppository form, if oral delivery is desired, the capsule can be supplied with an enteric coating. Such coatings are well known in the art as are the methods of enterically coating a capsule. The method of producing an enterically coated capsule is as follows. The drug delivery composition containing the active agent is prepared and this composition is then placed into a capsule. The capsule is then coated with an enteric coating solution. The enteric coating solution contains the polymeric enteric coating substance and solvents. The polymeric enteric coating substance is generally a pharmaceutically acceptable polymer that will dissolve upon contact with intestinal fluids, pH of about 5.5 to 7.0, but will not dissolve in the lower pH stomach fluids. Enteric polymer coatings are readily available commercially, such as the Eastman® C-A-P™ (cellulose acetate phthalate) and C-A-T (cellulose acetate trimellitate) enteric coating materials available from Eastman Chemical Products, Inc. Various techniques are known to apply the entire polymer coating such as spray coating or immersion coating and several layers of the enteric substance may be required.

The invention will now be illustrated by, but is not intended to be limited to, the following examples.

EXAMPLES

Example 1

Preparation of the Delivery Compositions

Various compositions were prepared containing the high level of PEG in the aqueous phase of the transparent, stable compositions, which were all liquids at room temperature. The compositions were prepared by simply admixing the various components in random order. No active agent was formulated with these compositions, however the addition of the active agent can be made without altering the character of the resulting composition.

The resulting compositions are represented graphically in the phase diagram shown in FIG. 1. Apex A represents 100 wt. % of the aqueous phase, apex B represents 100 wt. % of the oil phase, and apex C represents 100 wt. % of the surfactant and permeation enhancers. The shaded area represents compositions that produce transparent liquids.

The aqueous phase constituted 8.6 parts PEG 600, 1 part water, and 0.4 parts sorbitol. The oil phase constituted Captex 200 (propylene glycol dicaprylate/caprate having a fatty acid composition of caproic (4.1 wt. %), caprylic (68.29 wt. %), capric (27.4 wt. %), lauric and higher (0.2 wt. %), manufactured by Karlshams Lipid Specialties U.S.A.). The surfactant phase constituted 6 parts Imwitor 308 and 4 parts Tween 80 (polyoxyethylene sorbitan mono oleate, HLB=15, manufactured by Sigma Chemical). All parts being on a weight basis.

Example 2

Preparation of the Delivery Compositions

Figure 2:
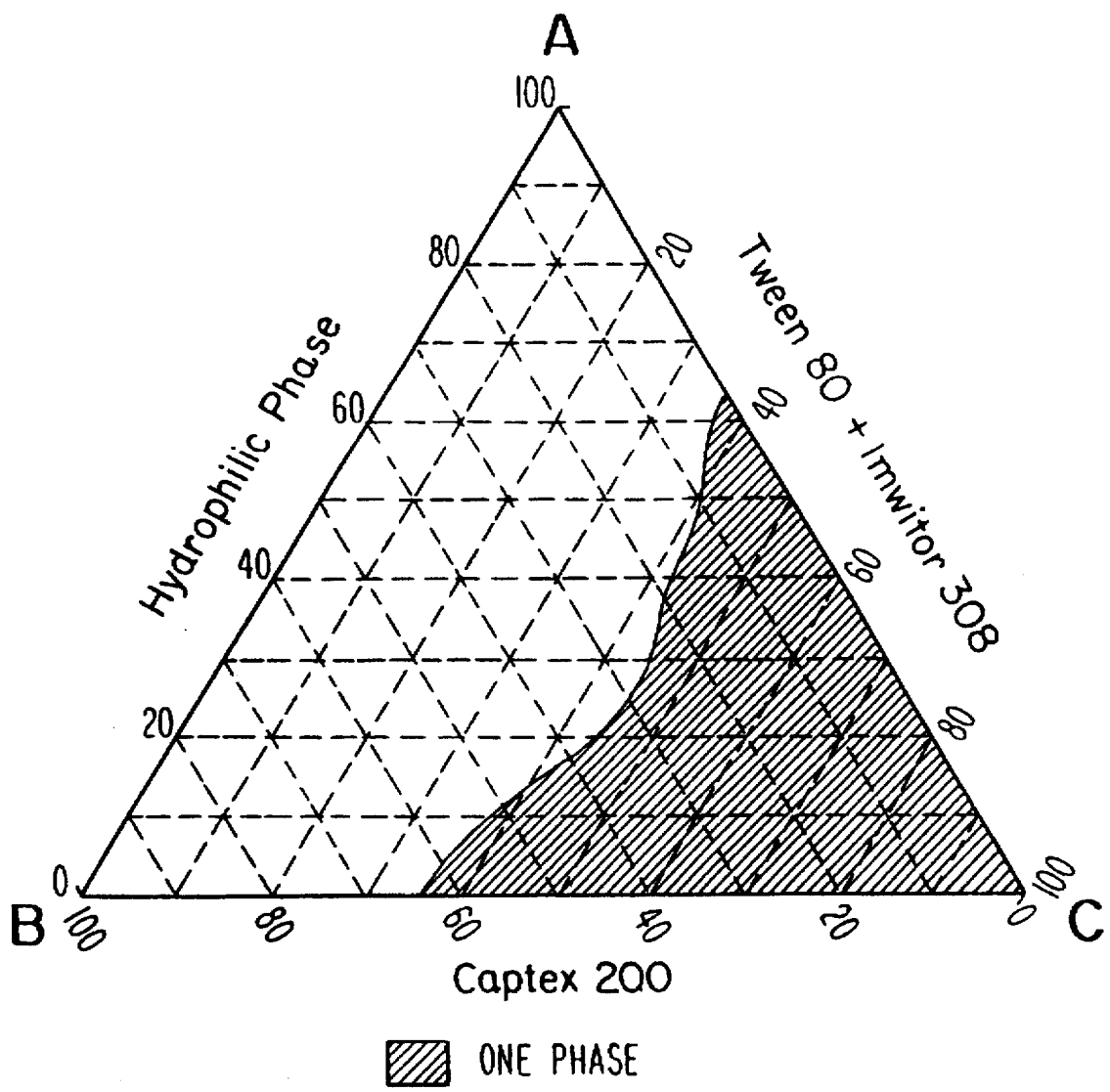
FIG. 2 is a phase diagram wherein the aqueous phase constituted 8.6 parts PEG 300, 1 part water, and 0.4 parts sorbitol. The oil phase constituted Captex 200 and the surfactant phase constituted 6 parts Imwitor 308 and 4 parts Tween 80.

The phase diagram as described in Example 1 was made except that the PEG 600 was replaced with PEG 300. The phase diagram is shown in FIG. 2.

Example 3

Preparation of the Delivery Compositions

Figure 3:
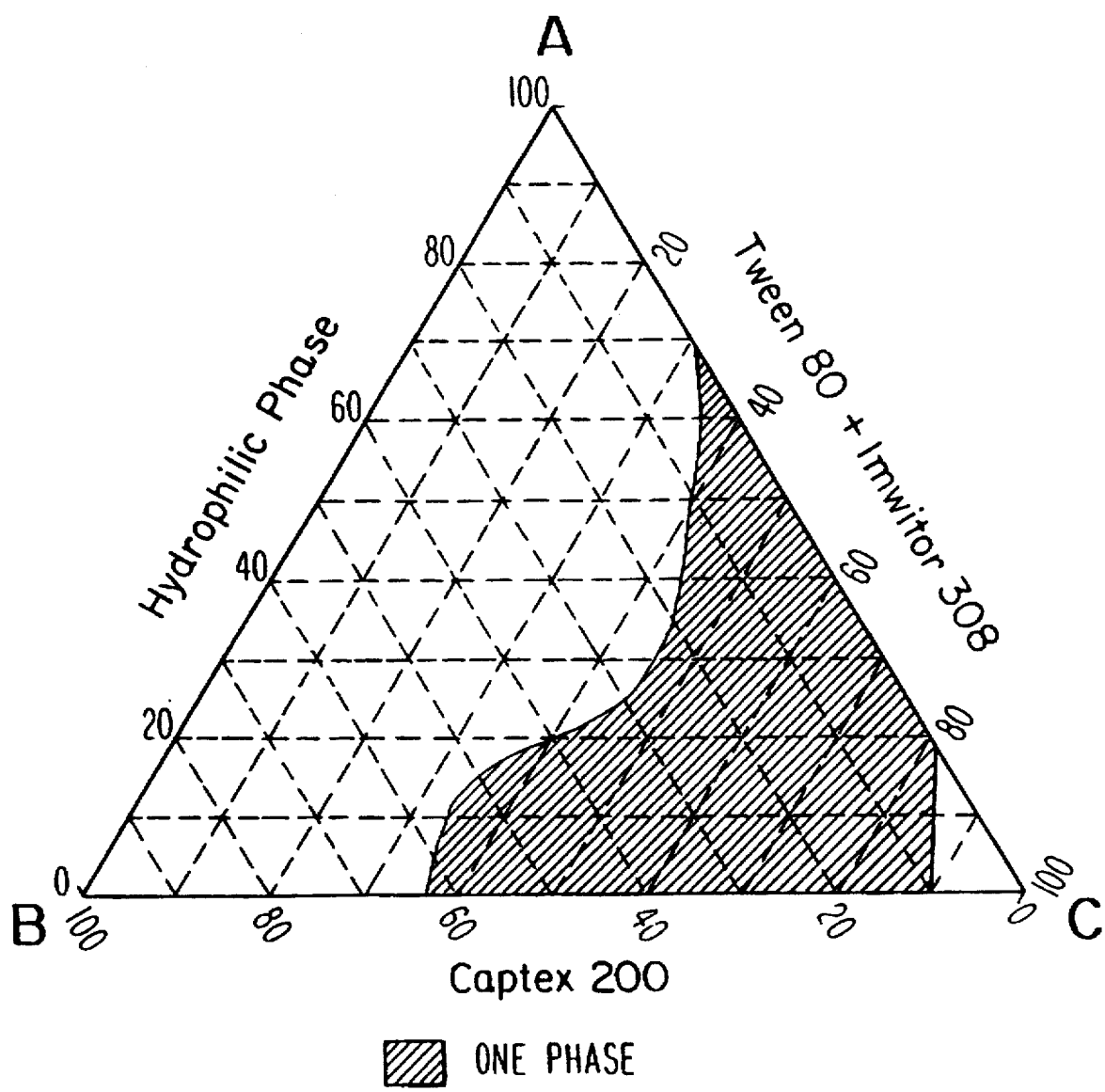
FIG. 3 is a phase diagram wherein the aqueous phase constituted 8.6 parts PEG 400, 1 part water, and 0.4 parts sorbitol. The oil phase constituted Captex 200 and the surfactant phase constituted 6 parts Imwitor 308 and 4 parts Tween 80.

The phase diagram as described in Example 1 was made except that the PEG 600 was replaced with PEG 400. The phase diagram is shown in FIG. 3.

Example 4

Preparation of the Delivery Compositions

Figure 4:
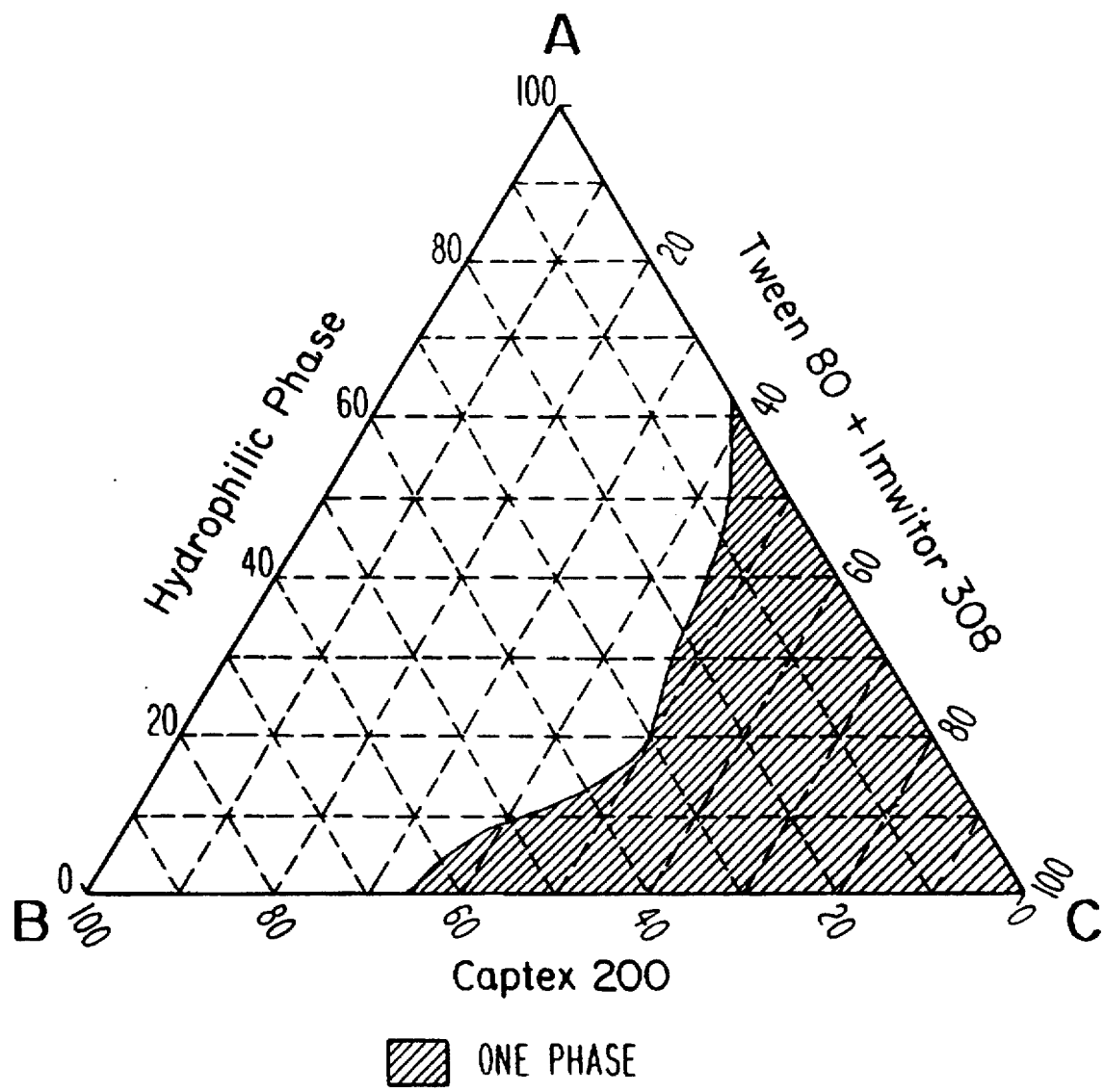
FIG. 4 is a phase diagram wherein the aqueous phase constituted 8.6 parts PEG 400, 1 part water, and 0.4 parts sorbitol. The oil phase constituted Captex 200 and the surfactant phase constituted 4 parts Imwitor 308 and 6 parts Tween 80.

The phase diagram as described in Example 3 was made except that the surfactant phase constituted 4 parts Imwitor 308 and 6 parts Tween 80. The phase diagram is shown in FIG. 4.

Example 5

Preparation of the Delivery Compositions

Figure 5:
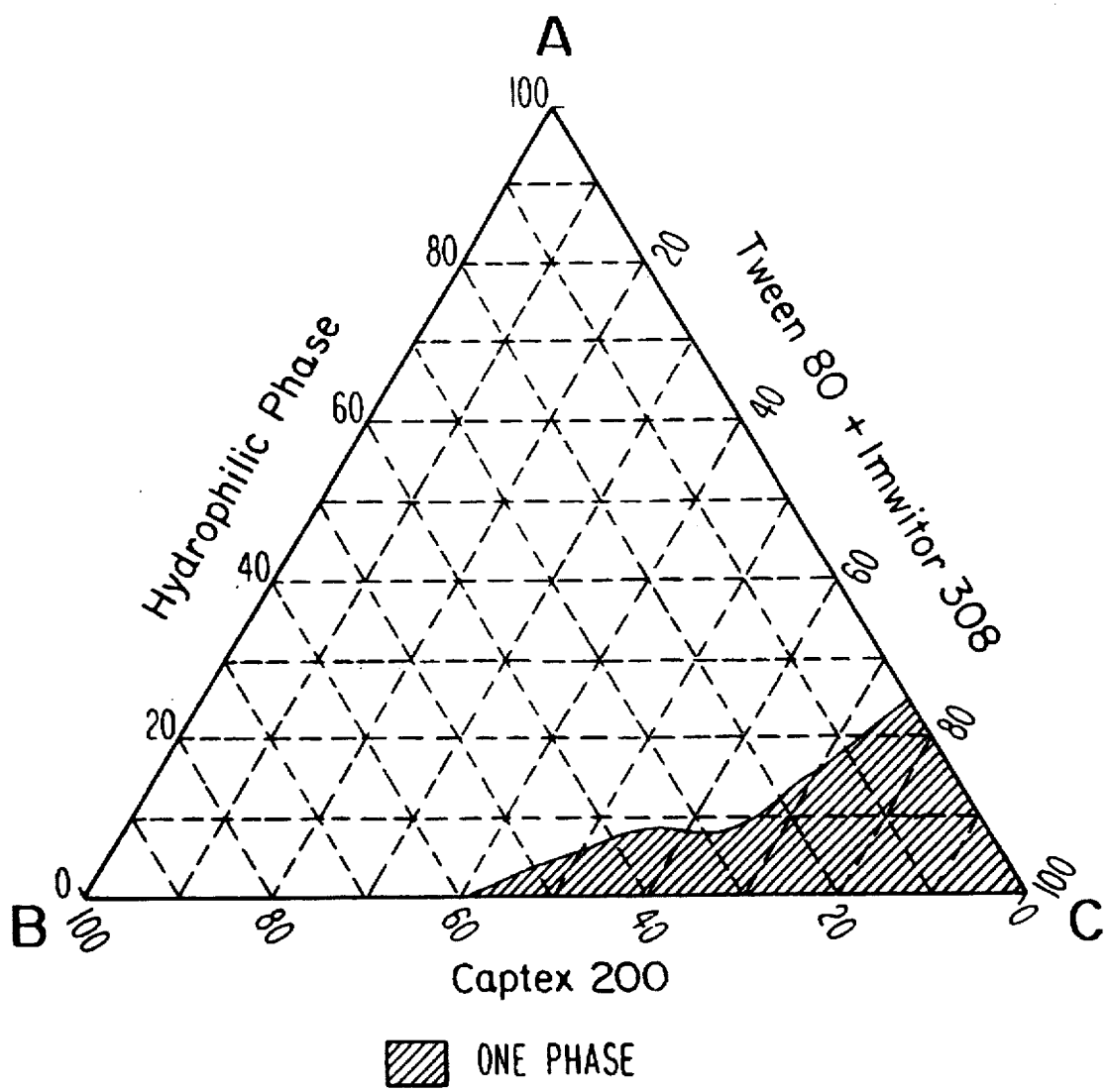
FIG. 5 is a phase diagrams wherein the aqueous phase constituted 8.0 parts PEG 400, 1 part water, and 1.0 parts sorbitol. The oil phase constituted Captex 200 and the surfactant phase constituted 6 parts Imwitor 308 and 4 parts Tween 80.

The phase diagram as described in Example 3 was made except that the aqueous phase constituted 8 parts PEG 400, 1 part sorbitol, and 1 part water. The phase diagram is shown in FIG. 5.

Example 6 dDAVP Dog Study

A drug delivery formulation able to solubilize the peptide dDAVP was prepared with the following composition:

| Example 6a | Composition (% w/w) |
|---|---|
| Captex 200 | 12.0 |
| Imwitor 308 | 28.8 |
| Tween 80 | 19.2 |
| PEG-400 | 32.4 |
| 1N HCl | 0.74 |
| Sorbitol | 1.60 |
| Water | 1.45 |
| 10 mg/ml dDAVP in 40 mM Acetate Buffer, pH 5.0 | 3.81 | dDAVP = 171 µg/g drug composition

Sorbitol was first dissolved in water and hydrochloric acid, then PEG-400, Tween 80, premelted Imwitor 308, and Captex 200 were added, and mixed until homogeneous. Meanwhile, dDAVP was dissolved in 40 mM acetate buffer, pH 5.0 solution. The drug solution was admixed with the Sorbitol/water/1N HCl/PEG-400/Captex 200/Tween 80/Imwitor 308 to form a transparent drug delivery composition. The same procedure was used to prepare the examples 6b, 6c and 6d with the following compositions (% w/w). In 6d, a drug-free acetate buffer solution was used.

| Examples | 6b | 6c | 6d |
|---|---|---|---|
| Captex 200 | 12.0 | 12.0 | 12.0 |
| Imwitor 308 | 28.8 | 28.8 | 28.8 |
| Tween 80 | 19.2 | 19.2 | 19.2 |
| PEG-400 | 32.4 | 32.4 | 32.4 |
| 1N HCl | 0.74 | 0.74 | 0.74 |
| Sorbitol | 1.60 | 1.60 | 1.60 |
| Water | 4.67 | 5.08 | 5.26 |
| 10 mg/ml dDAVP in 40 mM Acetate Buffer, pH 5.0 | 0.59 | 0.18 | 0.0 |
| dDAVP (µg/g) | 59 | 18 | 0.0 |

METHODOLOGY

DDAVP or desmopressin is a synthetic analogue of vasopressin, which has been demonstrated to have a longer half life in the bloodstream than the native vasopressin. Pharmacologically, it has an antidiuretic effect, and so has been useful in the treatment of biabetes insipidus and of pediatric nocturnal enuresis. It also elevates circulating levels of Factor VIII, and so has been used in treating certain forms hemophilia.

Male beagle dogs weighing 9–12 kg were used in all experiments. Prior to each study, all animals were fasted overnight but were allowed access to water ad libitum. The following study was used to demonstrate the advantage of the dDAVP-containing transparent liquid encapsulated in capsules of this invention:

1. Peroral administration: Enteric coated hard gelatin capsules, size 0el (0.78 ml) from CAPSUGEL, fill materials: 0.73 g of the drug delivery compositions containing:
   (i) 0 µg drug/g composition or 0 µg drug/capsule (Table 6D Example 6d)
   (ii) 18 µg drug/g composition or 13 µg drug/capsule (Table 6C, Example 6c)
   (iii) 59 µg drug/g composition or 43 µg drug/capsule (Table 6B, Example 6b)
   (iv) 171 µg drug/g composition or 125 µg drug/capsule (Table 6A, Example 6a)
2. Peroral administration: Enteric coated hard gelatin capsules, size 0el, fill materials: 171 µg dDAVP mixed with dextrose as filler (Table 6E).

3. Subcutaneous administration: 4 µg dDAVP/ml composition, 0.4 µg dDAVP/kg animal (Table 6F).

this invention at a dose of 10 µg/kg (125 µg/kg (125 µg/g, Table 6A).

TABLE 6.1

| | Compositions | | | | | | | | | | | |
|---|---|---|---|---|---|---|---|---|---|---|---|---|
| | A | | B | | C | | D | | E | | F | |
| Time | % | SEM | % | SEM | % | SEM | % | SEM | % | SEM | % | SEM |
| 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 |
| 2 | 59 | 12 | 68 | 10 | 21 | 9 | 16 | 19 | 15 | 12 | 59 | 14 |
| 5 | 54 | 14 | 64 | 8 | 29 | 4 | 39 | 25 | 13 | 9 | 58 | 15 |
| 10 | 36 | 22 | 70 | 15 | 23 | 7 | 53 | 18 | 13 | 15 | 61 | 15 |
| 15 | 37 | 26 | 75 | 13 | 26 | 6 | 31 | 15 | 22 | 7 | 63 | 14 |
| 30 | 81 | 24 | 77 | 15 | 25 | 9 | 47 | 16 | 12 | 11 | 69 | 12 |
| 45 | 86 | 26 | 74 | 16 | 32 | 9 | 57 | 15 | 17 | 11 | 46 | 17 |
| 60 | 75 | 25 | 57 | 24 | 27 | 8 | 42 | 12 | 12 | 11 | 81 | 17 |
| 90 | 103 | 27 | 69 | 12 | 15 | 7 | 13 | 24 | 10 | 12 | 69 | 12 |
| 120 | 74 | 20 | 63 | 11 | 14 | 7 | 28 | 15 | 0 | 17 | 91 | 21 |
| 150 | 81 | 9 | 35 | 18 | 6 | 9 | 21 | 19 | 0 | 2S | 82 | 20 |
| 180 | 60 | 10 | 59 | 14 | 6 | 6 | 13 | 16 | 0 | 12 | 83 | 22 |
| 240 | 34 | 11 | 66 | 19 | 4 | 10 | 8 | 16 | 0 | 26 | | |
| 300 | 48 | 9 | 79 | 11 | 1 | 8 | 19 | 16 | 0 | 8 | | |
| 360 | 35 | 11 | 77 | 12 | 11 | 5 | 29 | 11 | 0 | 16 | | |

Plasma Factor VIII levels following administration of dDAVP was used as a pharmacodynamic response to the drug. Maximum response to dDAVP was determined by measuring plasma Factor VIII response levels following subcutaneous administration of dDAVP (Table 6F). Administration of capsules containing compositions 6a through 6c provided dose response, composition 6d was a placebo control, dDAVP in dextrose provided a control is inert filler.

For studies involving capsule administration, a single capsule was given to each animal in each study. Blood samples were taken immediately prior to dDAVP administration (t=0), and at various times thereafter. Plasma levels of Factor VIII were determined using commercially available kits. Values are expressed as percent change in Factor VIII levels, relative to values obtained at t=0, and are shown as mean values±standard errors of the mean, in Table 6.1.

RESULTS

A dose-dependent increase in plasma Factor VIII levels was observed in dogs following administration of capsules containing 13, 43 and 125 micrograms (µg) dDAVP per transparent liquid capsule (Tables 6C, 6B and 6A). A similar degree of increase in Factor VIII levels was observed following administration of 43 µg/capsule and 125 µg/capsule (Tables 6B and 6A). In contrast to this, the response in Factor VIII levels after administration of dDAVP at 12 µg/capsule (Table 6C) was not significantly different from levels observed in placebo-treated animals (Table 6D).

The enhancement effect of the transparent liquid formulation can further be seen in Tables 6A and 6E, comparing administered using capsules containing dDAVP in transparent liquid and using capsules containing dDAVP in an admixture in which dextrose was used as an inert filler. In the latter case, the dDAVP showed virtually no response over the six hour test period (Table 6E). This was in marked contrast to the maximal response observed in animals that had been given capsules containing the dDAVP in the transparent liquid of this invention (table 6A).

The comparison of Tables 6F and 6A shows that dDAVP, given by subcutaneous injection at a does of 0.4 µg/kg, produced similar increase in Factor VIII levels as that which dDAVP was given orally in capsule with the formulation of Particle Size Measurement The particle size of composition 6d was determined using photon correlation spectroscopy. This composition had a viscosity of 106 centipoises, and a refractive index of 1.455 and appeared transparent to the naked eye.

A Brookhaven Instrument BI-9000AT with a 500 milliwatt laser source was used and provided a count rate of about 57 kilocounts/sec. The particle size was measured three times and the results were particle sizes of 1.2, 1.8, and 3 nanometers, with a polydispersity of 0.43, 0.1, and 0.72, respectively.

Example 7

Calcitonin Formulations

A formulation able to solubilize the peptide drug calcitonin in high concentration was prepared that was found to be compatible with gelatin capsules. This formulation maximized the concentration of the aqueous phase to solubilize more drug, but minimized the water concentration to confer compatibility with water soluble gelatin capsules. This was accomplished by replacing water in the polar phase with polyethylene glycol and sorbitol, yielding a formulation in which there would be no significant exchange of moisture or plasticizer between the formulation and the gelatin shell. The composition prepared is shown in Table 7.1:

TABLE 7.1

| Component | Concentration (% w/w) |
|---|---|
| Calcitonin | 0.12 |
| Water | 4.00 |
| Sorbitol | 1.60 |
| PEG-400 | 34.14 |
| Glacial Acetic Acid | 0.24 |
| 1N HCl | 0.018 |
| Imwitor 308 | 28.80 |
| Tween 80 | 19.20 |
| Captex 200 | 12.00 |

Calcitonin was first dissolved in water. Sorbitol was then added and dissolved, then a premixed solution of the acetic and hydrochloric acids and the PEG-400 was added, and mixed until homogeneous. Meanwhile, the Imwitor 308 was melted and admixed with the Tween 80 and Captex 200 to form a homogeneous mixture. The surfactant and oil mixture was admixed with the drug/water/sorbitol/PEG-400/acids mixture to form a transparent liquid formulation.

The calcitonin was found to be chemically stable in this formulation for at least two months.

Example 8

Capsule Compatibilty

The composition of Example 7 was prepared without the drug to test the stability of the composition in a gelatin capsule. The composition used is shown in Table 8.1:

TABLE 8.1

| Component | Concentrate: (% w/w) |
|---|---|
| Water | 4.0 |
| Sorbitol | 1.6 |
| PEG-400 | 34.14 |
| Glacial Acetic Acid | 0.24 |
| 1N HCl | 0.018 |
| Imwitor 308 | 28.80 |
| Tween 80 | 19.20 |
| Captex 200 | 12.00 |

The sorbitol was first dissolved in the water, then a premixed solution of the acetic and hydrochloric acids and the PEG-400 was added, and mixed until homogeneous. Meanwhile, the Imwitor 308 was melted and admixed with the Tween 80 and Captex 200 to form a homogeneous mixture. The drug/water/sorbitol/PEG-400/acids mixture to form a transparent liquid formulation.

This formulation was found to be compatible with, and stable when stored in, hard gelatin capsules from CAPSUGEL for at least two months. The capsules neither became brittle nor soft, and the formulation neither gained nor lost significant amounts of water to the capsule shell as shown in the Table 8.2. The formulation itself remained clear and homogeneous, as determined by visual observation.

TABLE 8.2

| Time (weeks) | 0 | 2 | 4 | 8 |
|---|---|---|---|---|
| [H$_2$O] (% w/w) | 4.9 | 5.07 | 4.60 | 4.31 |

Example 9

Calcein Bioavailability In Rats

Compositions A–F incorporating calcein as a marker were prepared for intraduodenal bioavailability studies in rats. Calcein solution, water, and sorbitol or glycerin were mixed together until the sorbitol or glycerin was dissolved, then the polyethylene glycol was added, and mixed until homogeneous. Meanwhile, the oil(s) and surfactants were mixed together to form a homogeneous mixture. The surfactant and oil mixture was admixed with the aqueous phase to form a transparent liquid formulation. In some cases, a small amount of 1N sodium hydroxide was added to bring the pH to the basic range before the liquid became transparent (compositions C, D and E).

Composition A

A transparent liquid containing 3 mM calcein as a marker was prepared with the following composition: Captex 200 (12% w/w), Imwitor 308 (29.8% w/w), Tween 80 (19.2% w/w), Polyethylene glycol 400 (32.4%/w), Sorbitol (1.6%/w), sterile water (3% w/w) and 100 mM Calcein solution in 10 mM Tris pH 7.4 (3% w/w).

Composition B

A transparent liquid containing 4.2 mM calcein was prepared with the following composition: Captex 200 (13% w/w), Imwitor 308 (26% w/w), Cremophor RH40 (26% w/w), Polyethylene glycol 400 (28% w/w), Glycerin (2.8% w/w), and 100 mM Calcein solution in 10 mM Tris pH 7.4 (4.2% w/w).

Composition C

A transparent liquid containing 2.9 mM calcein as was prepared with the following composition: Captex 200 (12% w/w), Imwitor 308 (28.8% w/w), Tween 80 (22.3% w/w), Glycocholic acid (1.9% w/w), Sodium Taurocholate (1.9% w/w), Polyethylene glycol 600 (31% w/w), Glycerin (3.1% w/w), sterile water (1.2% w/w), 1N Sodium hydroxide (0.7% w/w), and 100 mM Calcein solution in 10 mM Tris pH 7.4 (2.9% w/w).

Composition D

A transparent liquid containing 3.0 mM calcein as was prepared with the following composition: Captex 200 (11.5% sw/w), Imwitor 308 (23.4% w/w), Tween 80 (21.8% w/w), Glycocholic acid (3.7% w/w), Sodium Taurocholate (3.7% w/w), Polyethylene glycol 600 (28.7% w/w), Glycerin (1.3% w/w), sterile water (1.5% w/w'), 1N Sodium hydroxide (1.4% w/w), and 100 mM Calcein solution in 10 mM Tris pH 7.4 (3% w/w).

Composition E

A transparent liquid containing 1.5 mM Calcein as a marker was prepared with the following composition: Captex 200 (7% w/w), Cod liver Oil Methyl ester (5% w/w), Imwitor 308 (28.6%/w), Tween 80 (19.1% w/w), Polyethylene glycol 400 (34% w/w), Sorbitol (1.6% w/w), sterile water (2.9% w/w), 1N NaOH (0.2% w/w), and 100 mM Calcein solution in 10 mM Tris pH 7.4 (1.5% w/w).

Composition F

A transparent liquid containing 2.9 mM calcein as was prepared with the following composition: Captex 200 (10% w/w), Imwitor 308 (25% w/w), Glycocholic acid (5% w/w), Sodium Taurocholate (5% w/w), Linoleic acid (20% w/w), Polyethylene glycol 600 (29% w/w), Sorbitol (1.5% w/w), and 100 mM Calcein solution in 10 mM Tris pH 7.4 (4.5% w/w)

Methodology

Formulations in examples A–F were dosed intraduodenally to assess the bioavailability of calcein (5(6)-carboxyfluorescein, MW 623) using an unconscious rat model (Walker et al., Life Sciences, 47, 29–36, 1990), and compared with that obtained when calcein was dosed as a buffer solution. The concentrations of the calcein in plasma was measured using fluorescence spectroscopy. The dosing level was 2.5 µmol calcein/kg animal. The results for Compositions A–F are given in the following Table 9.1:

TABLE 9.1

| | Calcein Bioavailability | | |
|---|---|---|---|
| EXAMPLE | # Rats | Result | SEM |
| A | 10 | 27.6 | 4.8 |
| B | 5 | 25.8 | 7.1 |
| C | 12 | 39.7 | 6.8 |
| D | 4 | 35.4 | 1.5 |
| E | 4 | 33.4 | 13.1 |
| F | 5 | 39.5 | 5.6 |
| Buffer | 5 | 1.3 | 0.5 |

Example 10

Calcitonin bioavailability in rats

Compositions A–C incorporating calcitonin were prepared for intraduodenal bioavailability studies in rats. The bioavailability of calcitonin (used in the treatment of hypercalcemia by lowering $Ca^{+2}$ serum levels) was determined using an unconscious rat model.

Composition A

A transparent liquid containing about 30 µg/ml calcitonin was prepared with the following composition: Captex 200 (11.4% w/w), Imwitor 308 (23.3% w/w), Tween 80 (21.7% w/w), Glycocholic acid (3.7% w/w), chenodeoxycholic acid (3.7% w/w), PEG 600 (28.6% w/w), Glycerin (1.3% w/w), acetic acid (0.53% w/w), 1N NaOH (1.4% w/w), 750 mcg/ml calcitonin solution (3.9% w/w) and water (4.4% w/w). Two other similar formulations with about 10 µg/ml and 3 µg/ml calcitonin were prepared by replacing part of the calcitonin solution with water.

Composition B

A transparent liquid containing about 30 µg/ml calcitinin was prepared with the following composition: Captex 200 (11.7% w/w), Imwitor 308 (28% w/w), Tween 80 (18.7% w/w), Molecusol (β-cyclodextrin) (3% w/w) PEG 400 (31.3% w/w), sorbitol (1.7% w/w), 1 n HCl (0.33% w/w), 750 mcg/ml calcitonin solution (3.9% w/w), and water (1.43% w/w). Two other similar formulations with about 10 µg/ml and about 3 µg/ml calcitonin were prepared by replacing part of the calcitonin solution with water.

Composition C

A transparent liquid containing about 30 µg/ml calcitonin was prepared with the following composition: Captex 200 (11.7% w/w), Imwitor 308 (28% w/w), Polyoxyethylene 9 Lauryl Ether (18.7% w/w), PEG 1000 (31% w/w), sorbitol (1.7% w/w), 750 mcg/ml calcitonin solution (3.9% w/w), and water (5.1% w/w). Two other similar formulations with about 10 µg/ml and about 3 µg/ml calcitonin were prepared by replacing part of the calcitonin solution with water.

Methodology

Fasted rats (male Sprague-Dawley; 87–106 g) were anaesthetized with i.p. pentobarbital. An incision in the neck was made to reveal the jugular vein. A catheter was inserted into the jugular vein to collect blood samples for calcium analysis. An incision was made into the peritoneal cavity and the duodenum was exposed. A purse-string suture was introduced into the surface of the duodenum.

The animals were dosed intraduodenally at 1 ml per kg body weight and intravenously with 2 ml per kg body weight and then flushed with 100 µl of saline. Therefore, the intraduodenal administration was about 3 µg, 10 µg, and 30 µg per kg animal body weight and the intraveneous injection (5 i.u. calcitonin=1 µg at 3 i.u./ml) was about 1.2 µg/kg body weight.

After the formulation was introduced, the purse-string suture was tightened as the syringe needle was withdrawn to prevent leakage of the formulation into the peritoneal cavity.

The peritoneum was closed with surgical staples and the animals were kept anaesthetized through the duration of the experiment. Blood samples (50 to 200 µl) were taken periodically during the course of the experiment. The blood samples were used to prepare serum which was used to determine serum $Ca^{+2}$ (free ionized calcium) levels using Beckman 700 calcium clinical assay kits. The serum calcium levels are reported in Table 10.1 are in units of mg/dL. The number of rats for each group is given as the (#) value.

TABLE 10.1

Calcium Assay Results

| Administration/ Concentration | Time (hr.) | A Mean | A SEM (#) | B Mean | B SEM (#) | C Mean | C SEM (#) |
|---|---|---|---|---|---|---|---|
| IV | 0 | 6.7 | 0.3 (3) | 6.7 | 0.3 (3) | 6.5 | 0.3 (4) |
|  | 1 | 5.3 | 0.3 (3) | 6.0 | 0.6 (3.) | 5.2 | 0.2 (4) |
|  | 3 | 3.7 | 0.7 (3) | 5.3 | 0.3 (3) | 5.2 | 0.2 (4) |
| ID 3 mg/ml | 0 | 6.5 | 0.3 (6) | 6.7 | 0.2 (17) | 7.0 | 0.8 (5) |
|  | 1 | 5.8 | 0.2 (6) | 6.1 | 0.1 (7) | 6.4 | 0.7 (.5) |
|  | 3 | 6.3 | 0.5 (6) | 6.3 | 0.2 (7) | 6.4 | 0.7 (5) |
| ID 10 mg/ml | 0 | 6.7 | 0.3 (6) | 6.7 | 0.2 (8) | 7.0 | 1.3 (5) |
|  | 1 | 5.3 | 0.7 (6) | 5.5 | 0.3 (8) | 4.8 | 1.2 (5) |
|  | 3 | 5.2 | 1.2 (6) | 5.9 | 0.3 (8) | 5.6 | 1.6 (5) |
| ID 30 mg/ml | 0 | 7.0 | 0 (6) | 7.6 | 0.4 (7) | 7.3 | 1.1 (7) |
|  | 1 | 5.8 | 0.2 (6) | 5.7 | 0.3 (7) | 5.1 | 0.8 (7) |
|  | 3 | 5.5 | 0.3 (6) | 5.7 | 0.5 (7) | 4.9 | 0.6 (7) |

Example 11

Experiments can be carried out using rats with the 20 formulations of this invention to evaluate them as a vehicle for the delivery of RGD peptides, such as the peptide cyclo(S,S)-$N^\alpha$-acetyl-Cys-($N^\alpha$-methyl) Arg-Gly-Asp-Pen-$NH_2$.

Formulations

The test formulations are prepared according to the methods of the application, such as those set forth in FIGS. 1–5.

Test Method

Intravenous (i.v.) Administration:

Fasted rats are anesthetized with an intraperitoneal (i.p.) injection and surgically fitted with a jugular catheter (ACUC protocol #90-151). Rats are allowed to recover from the surgery for 1 day. Catherized rats are fasted for 18 hr prior to the experiment. Each rat receives either a 1 mg or 3 mg peptide/kg animal dose by lateral tail-vein administration. Blood samples of 0.5 ml aliquots are collected at 0, 1, 3, 5, 10, 15, 30, 45, 60, 90, 120, 150, and 180 min. The 0 min sample is taken 15 min prior to administration of the dose. Plasma is removed from the whole blood by centrifugation at 1600×g for 5 min, and then plasma is stored at −20° C. in 250 µl aliquots per sample. The blood pellet is reconstituted with 12.5 units heparinized saline and returned to the appropriate rat via the jugular catheter. After the experiment, rats are euthanized with i.v. administration of pentobarbital.

Intraduodenal (i.d.) Adminstration:

Fasted rats are administered an i.p. injection of anesthesia cocktail and surgically fitted with jugular and duodenal catheters. Rats are allowed to recover from the surgery for 4–5 days (ACUC protocol #91-055). Catherized rats are fasted 18–20 hr prior to the experiment. Each group of rats receives either 10 mg peptide/kg animal in each formulation (3.3 ml/kg) or 6.5 mg peptide/kg animal in each formulation (3.3 ml/kg). A saline control is administered to a group of rats containing 10 mg peptide/kg animal in a saline solution. Blood samples of 0.5 ml aliquots are collected via jugular catheter in heparinized eppendorf tubes at 0, 10, 30, 60, 120, 180, 240, and 1440 min. The 0 min sample is taken 15 min prior to administration of the dose by duodenal calheter. Plasma is collected for analysis and the blood returned to rats as described in the i.v. administration protocol. After 24 hr, rats are euthanized by i.v. administration of pentobarbital, exsanguinated, and a macroscopic observation of the intestinal tract is performed.

Post-Column HPLC Fluorescence Assay:

For samples and standards, plasma components are precipitated with 0.6 ml cetonitrile, and then pelleted by centrifugation at 16,000×g for 20 min. The supernatant is removed, and then dried to powder under $N_2$ at 40° C. Powder is dissolved in 0.5 ml 1% TFA solution, and then processed by solid-phase extraction procedure (SPEP). SPEP is as follows: 1) condition 1 ml $C_{18}$ columns with methanol, and then rinse columns with 1 ml water, 2) standards and samples are applied to columns, and then rinsed twice with 1 ml water, 3) standards and samples are collected in tubes upon elution from column with methanol by two 0.5 ml aliquots. The samples and standards are dried to powder under $N_2$ at 40° C., and then dissolved in 100 µl of 10% methanol: 90% ultrapure water solution. Standards and samples are placed in HPLC vials. Vials with standards are placed before and after vials containing the samples for HPLC analysis. For the peptide standards, an aliquot is injected for analysis based on the concentration of the standard as follows: 50 µl aliquot is injected for analysis by post-column fluorescence detection. Fluorescence chromatography data are collected and integrated using Nelson Chromatography Data System. The peak area ratio (Y) and peptide standard concentration (X) are used to determine the slope of a line which is forced through the origin from the equation: slope=(sum of X*Y)/(sum of $X^2$). The slope represents the relationship between peak area ratio and peptide plasma concentration for the samples.

Results

The area under the plasma concentration curve (AUC) is determined for each test group. The percentage bioavailability is determined by the equation with the average AUC from iv administration: $[(AUC_{id}/AUC_{iv})*(mg/kg_{iv}/mg/kg_{id})]*100$.

Example 12

Studies can be conducted to determine whether the formulations of the present invention can enhance the bioavailability of the proteinaceous material disclosed in U.S. Pat. No. 4,703,036 (N-methyl-D-phenylalanyl-L-propyl-L-argininal sulfate), which is incorporated herein in its entirety, which is a tripeptide-aldehyde derivative having a molecular weight of about 515 (CAS No. 126721-07-1), the peptide having anticoagulant activity.

The formulation can be prepared according to the compositions set forth in FIGS. 1–5 with about 0.7% wt. peptide. A control composition containing the peptide in saline is also prepared. Both preparations contain 5 mg peptide/ml composition.

Male Fisher 344 rats are anesthetized with methoxyflurane, and a midline abdominal incision is made to expose the intestine and 5 mg peptide/kg animal in the form of the microemulsion is injected into the duodenal lumen distally. The injection site and surgical incision site are closed with surgical adhesive and the animals are allowed to recover. Blood samples are collected in heparinized Vacutainer tubes via cardiac puncture at appropriate times. Blood is reduced to plasma and plasma samples are analyzed for the peptide by HPLC with UV detection.

The results are determined by calculating the area under the curve (AUC) for the inventive formulations compared to the saline.

What is claimed is:

1. A stable, transparent drug delivery composition suitable for storage and administration of biologically active materials, comprising:
   (a) a delivery composition comprising:
      (1) from about 1 to about 80 weight percent of a pharmaceutically acceptable oil phase;
      (2) from about 3 to about 98 weight percent surfactant;
      (3) from about 2 to about 60 weight percent polyethylene glycol;
      (4) from about 0.5 to about 15 weight percent water; and
   (b) a therapeutically effective amount of a biologically active material having an octanol:water partition coefficient of less than about 0.1;
   provided that the composition does not contain a mixture of cholesterol and phospholipid, and wherein the ratio of the polyethylene glycol to water is at least 2:1.

2. The drug delivery composition of claim 1 wherein the delivery composition further comprises at least one plasticizer comprising sorbitol, mannitol, or glycerin, said plasticizer being present in an amount of from about 0.5 to about 10 weight percent of the delivery composition.

3. The drug delivery composition of claim 2 wherein the drug delivery composition is contained in a capsule and the ratio of the polyethylene glycol to water is from about 4:1 to about 99:1, and said plasticizer comprises sorbitol, mannitol, or glycerin.

4. The encapsulated drug delivery composition of claim 3 wherein the capsule is a gelatin or starch capsule.

5. The encapsulated drug delivery composition of claim 4 wherein the active material comprises a protein, peptide, or polysaccharide.

6. The encapsulated drug delivery composition of claim 5 wherein the surfactant component is a mixture of surfactants comprising a low HLB surfactant, said low HLB surfactant having an HLB below 10 and a high HLB surfactant, said high HLB surfactant having an HLB above 10, and wherein the low HLB surfactant comprises a $C_{9-13}$ monoglyceride.

7. The encapsulated drug delivery composition of claim 5 wherein the active material comprises a medicament which is selected from the group consisting of erythropoietin, insulin, a growth hormone, calcitonin, growth colony stimulating factors, RGD peptides, hematoregulatory peptides, collagenase inhibitors, angiotensin inhibitors, heparins, hypothalamic releasing peptides, tissue plaminogen activators, artial natriuretic peptides, tumor necrosis factor, vasopressin, a vasopressin antagonist, t-PA, vamprire bat plasminogen amplifier, urokinase, streptokinase, interferon and interleukin, in a biologically effective, therapeutic, non-toxic quantity.

8. The encapsulated drug delivery composition of claim 5 wherein the active material comprises a medicament which is selected from the group consisting of insulins, growth hormones, fibrinogen antagonists and calcitonins.

9. A stable, transparent delivery composition, comprising:
   (a) from about 5 to about 70 weight percent of a pharmaceutically acceptable oil phase;
   (b) from about 10 to about 80 weight percent surfactant;
   (c) from about 5 to about 60 weight percent of an aqueous phase comprising from about 60 to about 95 weight percent polyethylene glycol, from about 2 to about 30 weight percent water, and from about 1 to about 15 weight percent plasticizer comprising sorbitol, mannitol, glycerin, sucrose, fructose, glucose, or lactose; and
   wherein the ratio of the polyethylene glycol to water is at least 2:1, provided that the composition does not contain a mixture of cholesterol and phospholipid.

10. The delivery composition of claim 9 wherein the polyethylene glycol to water ratio is from about 4:1 to about 99:1, and said plasticizer comprises sorbitol, mannitol, or glycerin.

11. The delivery composition of claim 10 wherein the aqueous phase consists of said water, polyethylene glycol, and plasticizer.

12. The delivery composition of claim 11 further comprising a therapeutically effective amount of a biologically active, therapeutic material having an octanol:water partition coefficient of less than 0.1.

13. The drug delivery composition of claim 12 wherein the drug delivery composition is contained in a hard gelatin, soft gelatin, or starch capsule.

14. The encapsulated drug delivery composition of claim 13 wherein the biologically active material comprises a protein, peptide, or polysaccharide.

15. The encapsulated drug delivery composition of claim 14 wherein the surfactant component is a mixture of surfactants comprising a low HLB surfactant, said low HLB surfactant having an HLB below 10 and a high HLB surfactant, said high HLB surfactant having an HLB above 10, and wherein the low HLB surfactant comprises a $C_{9-13}$ monoglyceride.

16. The encapsulated drug delivery composition of claim 14 wherein the active material comprises a medicament which is selected from the group consisting of erythropoietin, insulin, a growth hormone, calcitonin, growth colony stimulating factors, RGD peptides, hematoregulatory peptides, collagenase inhibitors, angiotensin inhibitors, heparins, hypothalamic releasing peptides, tissue plaminogen activators, artial natriuretic peptides, tumor necrosis factor, vasopressin, a vasopressin antagonist, t-PA, vamprire bat plasminogen amplifier, urokinase, streptokinase, interferon and interleukin, in a biologically effective, therapeutic, non-toxic quantity.

17. The encapsulated drug delivery composition of claim 14 wherein the active material comprises a medicament which is selected from the group consisting of insulins, growth hormones, fibrinogen antagonists and calcitonins.

18. The encapsulated drug delivery composition of claim 14 wherein the oil is selected from the group consisting of triglycerides having from 21 to 45 carbon atoms and propylene glycol diesters having from 15 to 40 carbon atoms.

19. A method of administering an encapsulated drug delivery composition, comprising:
providing a capsule within which is contained a drug delivery composition comprising:
(a) a delivery composition comprising:
(1) from about 5 to about 70 weight percent of an oil phase;
(2) from about 5 to about 60 weight percent of an aqueous phase consisting essentially of water, polyethylene glycol, and at least one plasticizer, said aqueous phase comprising from about 2 to about 30 weight percent water, from about 60 and 95 weight percent polyethylene glycol, and from about 1 to about 15 weight percent plasticizer comprising sorbitol, mannitol, or glycerin;
(3) from about 15 to about 75 weight percent of a surfactant mixture; and
(b) a therapeutically effective amount of a biologically active therapeutic material having an octanol:water partition coefficient of less than about 0.1; and provided that the delivery composition does not contain a mixture of cholesterol and phospholipid; and
administering said encapsulated drug delivery composition either orally, rectally, or vaginally to the body of an animal.

20. The method of claim 19 wherein said active material is either a protein, peptide, or polysaccharide.

21. The method of claim 20 wherein said administration is oral.

22. The method of claim 21 wherein the weight ratio of polyethylene glycol to water in said delivery composition is from 4:1 to 99:1.

23. The encapsulated drug delivery composition of claim 6 wherein said low HLB surfactant is present in an amount of from about 10 to about 40 weight percent of said delivery composition and said high HLB surfactant is present in an amount of from about 10 to about 40 weight percent of said delivery composition.

24. The encapsulated drug delivery composition of claim 23 wherein said delivery composition comprises from about 15 to about 55 weight percent polyethylene glycol.

25. The encapsulated drug delivery composition of claim 5 wherein said surfactant mixture comprises from 15 to 75 weight percent of said delivery composition.

26. The encapsulated drug delivery composition of claim 25 provided that said plasticizer does not comprise propylene glycol.

27. The encapsulated drug delivery composition of claim 7 provided that said plasticizer does not comprise propylene glycol.

28. The encapsulated drug delivery composition of claim 24 provided that said plasticizer does not comprise propylene glycol.

29. The encapsulated drug delivery composition of claim 15 wherein said low HLB surfactant is present in an amount of from about 10 to about 40 weight percent of said delivery composition and said high HLB surfactant is present in an amount of from about 10 to about 40 weight percent of said delivery composition.

30. The encapsulated drug delivery composition of claim 29 wherein said aqueous phase comprises from about 70 to about 90 weight percent polyethylene glycol, and the ratio of the polyethylene glycol to water is from about 5:1 to about 95:5.

31. The encapsulated drug delivery composition of claim 14 provided that said plasticizer does not comprise propylene glycol.

32. The encapsulated drug delivery composition of claim 16 provided that said plasticizer does not comprise propylene glycol.

33. The encapsulated drug delivery composition of claim 29 provided that said plasticizer does not comprise propylene glycol.

34. The method of claim 22 wherein the surfactant component of said delivery composition is a mixture of surfactants comprising a low HLB surfactant, said low HLB surfactant having an HLB below 10 and a high HLB surfactant, said high HLB surfactant having an HLB above 10, and wherein the low HLB surfactant comprises a $C_{9-13}$ monoglyceride.

35. The method of claim 34 wherein said low HLB surfactant is present in an amount of from about 10 to about 40 weight percent of said delivery composition and said nigh HLB surfactant is present in an amount of from about 10 to about 40 weight percent of said delivery composition.

36. The method of claim 35 wherein the active material comprises a medicament which is selected from the group consisting of erythropoietin, insulin, a growth hormone, calcitonin, growth colony stimulating factors, RGD peptides, hematoregulatory peptides, collagenase inhibitors, angiotensin inhibitors, heparins, hypothalamic releasing peptides, tissue plaminogen activators, artial natriuretic peptides, tumor necrosis factor, vasopressin, a vasopressin antagonist, t-PA, vamprire bat plasminogen amplifier, urokinase, streptokinase, interferon and interleukin, in a biologically effective, therapeutic, non-toxic quantity.

37. The method of claim 35 wherein the drug delivery composition is contained in a hard gelatin, soft gelatin, or starch capsule.

38. The method of claim 22 provided that said plasticizer does not comprise propylene glycol.

39. The method of claim 35 provided that said plasticizer does not comprise propylene glycol.

40. The drug delivery composition of claim 1 wherein the biologically active material comprises desmopressin.

41. The drug delivery composition of claim 3 wherein the biologically active material comprises desmopressin.

42. The drug delivery composition of claim 9 wherein the biologically active material comprises desmopressin.

43. The drug delivery composition of claim 10 wherein the biologically active material comprises desmopressin.

44. The method of claim 19 wherein the biologically active material comprises desmopressin.

45. The method of claim 44 wherein the administration is oral.

* * * * *

UNITED STATES PATENT AND TRADEMARK OFFICE
CERTIFICATE OF CORRECTION

PATENT NO. : 5,707,648
DATED : January 13, 1988
INVENTOR(S) : Yiv

It is certified that error appears in the above-identified patent and that said Letters Patent is hereby corrected as shown below:

Column 1, line 54, please delete "248" and insert therefor --240--.
Column 2, line 2, please delete "micelies" and insert therefor --micelles--.
Column 2, line 32, please delete "/" between the words "the" and "intestines".
Column 4, line 52, please delete "caprlic" and insert therefor --caprylic--.
Column 5, line 29, please delete "stabity" and insert therefor --stability--.
Column 7, line 7, please delete "hydrolyric" and insert therefor --hydroltic--.
Column 7, line 18, please delete "these" and insert therefor --those--.
Column 7, line 44, please delete "ptasticizer" and insert therefor --plasticizer--.
Column 9, line 57, please delete "PCl" and insert therefor --pCl--.
Column 10, line 62, please delete "pro" and insert therefor --Pro--.
Column 12, line 37, please delete "PTM" and insert therefor --PTH--.
Column 17, line 42, please delete "$\pm$" and insert therefor --+/---.
Column 18, Table 6.1, Time Column, row 6, please delete "i5" and insert therefor --15--.
Column 18, Table 6.1, Column E - SEM, row 12, please delete "2S" and insert therefor --25--.
Column 22, Table 10.1, Column B - SEM (#), row 4, please delete "(.3)" and insert therefor --(3)--.
Column 22, Table 10.1, Column B - SEM (#), row 8, please delete "(17)" and insert --(7)--.

UNITED STATES PATENT AND TRADEMARK OFFICE
CERTIFICATE OF CORRECTION

PATENT NO.  : 5,707,648
DATED       : January 13, 1988
INVENTOR(S) : Yiv

It is certified that error appears in the above-identified patent and that said Letters Patent is hereby corrected as shown below:

Column 22, Table 10.1, Column C - SEM (#), row 10, please delete "(.5)" and insert therefor --(5)--.
Column 22, line 32, please delete "20"
Col 30, line 24, please delete "nigh" and insert therefor --high--.
In the Sequence Listing:  Col. 23, line 47,
  (2) Information for SEQ ID No.1: (ix)(D)(first occurrence) please delete "cyclo (S,S)- N'-acetyl-Cys" and insert therefor --cyclo (S,S)- $N^\alpha$-acetyl-Cys--.
line 52 (2) Information for SEQ ID No.1: (ix)(D)(second occurrence) please delete "(N'-methyl)Arg" and insert therefor --($N^\alpha$-methyl)Arg--.
line 57 (2) Information for SEQ ID No.1: (ix)(D)(third occurrence) please delete "Pen-NH2" and insert therefor --Pen-$NH_2$--.
Col. 25, line 19,
  (2) Information for SEQ ID No.2: (ix)(D) please delete "cycle (S,S)- N'-acetyl-Cys" and insert therefor --cyclo (S,S)- $N^\alpha$-acetyl-Cys--.

Signed and Sealed this

Twentieth Day of October, 1998

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5 amino acid residues
        ( B ) TYPE: Amino Acid
        ( C ) STRANDEDNESS:
        ( D ) TOPOLOGY: Unknown ( i i ) MOLECULE TYPE: Peptide ( i x ) FEATURE:
        ( A ) NAME/KEY: Modified-site
        ( B ) LOCATION: 1
        ( D ) OTHER INFORMATION: cyclo (S,S)- N'-acetyl-Cys ( i x ) FEATURE:
        ( A ) NAME/KEY: Modified-site
        ( B ) LOCATION: 2
        ( D ) OTHER INFORMATION: (N'- methyl)Arg ( i x ) FEATURE:
        ( A ) NAME/KEY: Modified-site
        ( B ) LOCATION: 5
        ( D ) OTHER INFORMATION: Pen-NH2 wherein Pen is
            penicillamine ( x i ) SEQUENCE DESCRIPTION: SEQ ID NO:1:

Cys  Arg  Gly  Asp  Xaa
                                 5

( 2 ) INFORMATION FOR SEQ ID NO:2:

( i ) SEQUENCE CHARACTERISTICS:
        ( A ) LENGTH: 7 amino acid residues
        ( B ) TYPE: Amino Acid
        ( C ) STRANDEDNESS:
        ( D ) TOPOLOGY: Unknown ( i i ) MOLECULE TYPE: Peptide ( i x ) FEATURE:
        ( A ) NAME/KEY: Modified-site
        ( B ) LOCATION: 1
        ( D ) OTHER INFORMATION: cyclo (S,S)- N'-acetyl-Cys ( i x ) FEATURE:
        ( A ) NAME/KEY: Modified-site
        ( B ) LOCATION: 3
        ( D ) OTHER INFORMATION: 4,4'- dimethylthiazolidine-
            5-carboxylic acid ( i x ) FEATURE:
        ( A ) NAME/KEY: Modified-site
        ( B ) LOCATION: 4
        ( D ) OTHER INFORMATION:para- aminomethylphenylalanine ( x i ) SEQUENCE DESCRIPTION: SEQ ID NO:2:

Cys  Asn  Xaa  Xaa  Gly  Asp  Cys
                              5

( 2 ) INFORMATION FOR SEQ ID NO:3:

( i ) SEQUENCE CHARACTERISTICS:
        ( A ) LENGTH: 5 amino acid residues
        ( B ) TYPE: Amino Acid
        ( C ) STRANDEDNESS:
        ( D ) TOPOLOGY: Unknown ( i i ) MOLECULE TYPE: Peptide ( x i ) SEQUENCE DESCRIPTION: SEQ ID NO:3:

Tyr  Gly  Gly  Phe  Leu
                              5

( 2 ) INFORMATION FOR SEQ ID NO:4:

( i ) SEQUENCE CHARACTERISTICS:
        ( A ) LENGTH: 5 amino acid residues
        ( B ) TYPE: Amino Acid
        ( C ) STRANDEDNESS:
        ( D ) TOPOLOGY: Unknown ( i i ) MOLECULE TYPE: Peptide ( x i ) SEQUENCE DESCRIPTION: SEQ ID NO:4:

Tyr  Gly  Gly  Phe  Met
                              5

( 2 ) INFORMATION FOR SEQ ID NO:5:

( i ) SEQUENCE CHARACTERISTICS:
        ( A ) LENGTH: 10 amino acid residues
        ( B ) TYPE: Amino Acid
        ( C ) STRANDEDNESS:
        ( D ) TOPOLOGY: Unknown ( i i ) MOLECULE TYPE: Peptide ( i x ) FEATURE:
  ( A ) NAME/KEY: Modified-site
  ( B ) LOCATION: 1
  ( D ) OTHER INFORMATION: pyroglutamic acid ( x i ) SEQUENCE DESCRIPTION: SEQ ID NO:5:

Xaa His Trp Ser Tyr Gly Leu Arg Pro Gly
              5                       10